(12) United States Patent
Wang

(10) Patent No.: US 11,579,219 B2
(45) Date of Patent: Feb. 14, 2023

(54) SYSTEMS AND METHODS FOR ESTIMATING COMPLEX RADIOFREQUENCY FIELDS IN A MAGNETIC RESONANCE IMAGING

(71) Applicant: University of Cincinnati, Cincinnati, OH (US)

(72) Inventor: Jinghua Wang, Mason, OH (US)

(73) Assignee: University of Cincinnati, Cincinnati, OH (US)

(*) Notice: Subject to any disclaimer, the term of this patent is extended or adjusted under 35 U.S.C. 154(b) by 355 days.

(21) Appl. No.: 16/753,990

(22) PCT Filed: Oct. 3, 2018

(86) PCT No.: PCT/US2018/054154
§ 371 (c)(1),
(2) Date: Apr. 6, 2020

(87) PCT Pub. No.: WO2019/070848
PCT Pub. Date: Apr. 11, 2019

(65) Prior Publication Data
US 2020/0393526 A1 Dec. 17, 2020

Related U.S. Application Data

(60) Provisional application No. 62/568,845, filed on Oct. 6, 2017.

(51) Int. Cl.
*G01V 3/00* (2006.01)
*G01R 33/24* (2006.01)
(Continued)

(52) U.S. Cl.
CPC ............ *G01R 33/246* (2013.01); *A61B 5/055* (2013.01); *G01R 33/288* (2013.01);
(Continued)

(58) Field of Classification Search
CPC ............. G01R 33/543; G01R 33/5659; G01R 33/3415; G01R 33/36; A61B 5/055
(Continued)

(56) References Cited

U.S. PATENT DOCUMENTS 6,559,642 B2   5/2003  King
6,697,661 B2   2/2004  Raghavan et al.
(Continued)

FOREIGN PATENT DOCUMENTS

| CN | 106108899 A | * 11/2016 | ........... A61B 5/0507 |
|---|---|---|---|
| WO | 2016183572 A1 | 11/2016 | |
| WO | 2018136705 A1 | 7/2018 | |

OTHER PUBLICATIONS

International Search Report for PCT/US2018/054154 dated Dec. 26, 2018.
(Continued)

*Primary Examiner* — Walter L Lindsay, Jr.
*Assistant Examiner* — Frederick Wenderoth
(74) *Attorney, Agent, or Firm* — Dinsmore & Shohl

(57) ABSTRACT

A method and apparatus for determining spatial distribution of a complex radio frequency (RF) of both transmit field and receive sensitivity a magnetic resonance imaging (MRI) system. The method includes estimation of the absolute phase of transmit field using a reference transmit coil or array coils with minimal absolute phase. The method and apparatus include estimation of complex receive sensitivity of a transceiver coil using the complex transmit field of the transceiver coil or array coils.

19 Claims, 10 Drawing Sheets

(51) Int. Cl.
*A61B 5/055* (2006.01)
*G01R 33/28* (2006.01)
*G01R 33/561* (2006.01)
*G01R 33/565* (2006.01)

(52) U.S. Cl.
CPC ...... *G01R 33/5611* (2013.01); *G01R 33/5615* (2013.01); *G01R 33/5659* (2013.01)

(58) Field of Classification Search
USPC ........................................................ 324/309
See application file for complete search history.

(56) References Cited

U.S. PATENT DOCUMENTS

| | | | |
|---|---|---|---|
| 6,949,928 B2 | 9/2005 | Gonzalez Ballester et al. | |
| 7,064,547 B1 | 6/2006 | King et al. | |
| 7,187,791 B2 | 3/2007 | Ikezaki | |
| 7,254,435 B2 | 8/2007 | Zhang et al. | |
| 7,375,523 B1 | 5/2008 | Hancu | |
| 7,492,153 B2 | 2/2009 | Brau et al. | |
| 7,777,487 B2 | 8/2010 | Ying et al. | |
| 8,076,938 B2 | 12/2011 | Brau et al. | |
| 8,093,894 B2 | 1/2012 | Machida et al. | |
| 8,334,694 B2 | 12/2012 | Tan et al. | |
| 8,379,951 B2 | 2/2013 | Lustig et al. | |
| 8,502,538 B2 | 8/2013 | Dannels et al. | |
| 9,146,293 B2 | 9/2015 | Wang et al. | |
| 9,229,074 B2 | 1/2016 | Voigt et al. | |
| 9,316,707 B2 | 4/2016 | Khalighi et al. | |
| 9,759,786 B2 | 9/2017 | Asaba et al. | |
| 2002/0171422 A1* | 11/2002 | King | G01R 33/3415 324/309 |
| 2004/0155652 A1 | 8/2004 | Sodickson | |
| 2005/0200357 A1 | 9/2005 | Pruessmann et al. | |
| 2006/0106299 A1 | 5/2006 | Uchizono et al. | |
| 2007/0182410 A1 | 8/2007 | Niemi et al. | |
| 2009/0278536 A1 | 11/2009 | Winkelmann et al. | |
| 2010/0239142 A1* | 9/2010 | Dannels | G06T 11/003 324/309 |
| 2011/0133734 A1* | 6/2011 | Freytag | G01R 33/3614 324/318 |
| 2013/0082708 A1 | 4/2013 | Yokosawa et al. | |
| 2013/0099786 A1 | 4/2013 | Huang et al. | |
| 2014/0088899 A1 | 3/2014 | Liu et al. | |
| 2014/0103925 A1* | 4/2014 | Hancu | G01R 33/48 324/309 |
| 2014/0300354 A1 | 10/2014 | He et al. | |
| 2015/0105031 A1* | 4/2015 | Colombi | H04B 17/102 455/73 |
| 2015/0362574 A1 | 12/2015 | Wu et al. | |
| 2016/0054262 A1 | 2/2016 | Sodickson et al. | |
| 2016/0077182 A1 | 3/2016 | Wang et al. | |
| 2018/0246178 A1* | 8/2018 | Wang | G01V 3/14 |

OTHER PUBLICATIONS

Martin Uecker, et al., "Estimating Absolute-Phase Maps Dsing ESPIRiT and Virtual Conjugate Coils," Magnetic Resonance in Medicine 77:1201-1207 (2017).

Ulrich Katscher, et al., "Determination of Electric Conductivity and Local SAR Via B1 Mapping," IEEE Transactions On Medical Imaging, vol. 28, No. 9, Sep. 2009.

Charles A. McKenzie, et al., "Self-Calibrating Parallel Imaging With Automatic Coil Sensitivity Extraction," Magnetic Resonance in Medicine 47:529-538 (2002).

European Search Report pertaining to Application No. 18864141.9 dated May 27, 2021.

Gurler et al., "CR-MREPT Using Multichannel Receive Coil", Proceedings of the International Society for Magnetic Resonance in Medicine, ISMRM Joint Annual Meeting, No. 3247, Apr. 28, 2014.

Sodickson et al., "Local Maxwell Tomography Using Transmit-Receive Coil Arrays for Contact-Free Mapping of Tissue Electrical Properties and Determination of Absolute RF Phase", Proc. Intl. Soc. Mag. Reson. Med, vol. 20, Apr. 21, 2012.

Wang et al., "Absolute Phse of Radio-frequency Tramit Field B1+ for a Dual Transmit Coil System", Proceedings of the International Society for Magnetic Resonance in Medicine, ISMRM, 27th Annual Meeting and Exhibition, No. 4505, Apr. 26, 2019.

Zhang et al., "Complex B1 Mapping and Electrical Properties Imaging of the Human Brain Using a 16-channel Transceiver Coil at 7T", Magnetic Resonance in Medicine, vol. 69, No. 5, pp. 12585-1296, Jun. 12, 2012.

* cited by examiner

SYSTEMS AND METHODS FOR ESTIMATING COMPLEX RADIOFREQUENCY FIELDS IN A MAGNETIC RESONANCE IMAGING

CROSS-REFERENCE TO RELATED APPLICATIONS

This application is a national phase of International Application No. PCT/US2018/054154 filed on Oct. 3, 2018 which claims the benefit of U.S. Provisional Application No. 62/568,845 filed on Oct. 6, 2017, the entire contents of which are incorporated by reference.

BACKGROUND

Magnetic resonance imaging (MRI) is one of the most important modern medical imaging modalities to generate high-resolution anatomical and functional images. It has far less risk of side effects than most other imaging modalities such as radioscopy with x-rays or computed tomography because patient and medical personal are not subjected to ionizing radiation exposure in the procedure. The use of MRI has grown very fast. Every year, more than 30 million MRI scans are performed in the United States; more than 60 million MRI scans are performed worldwide. Doctors often recommend MRI for the diagnoses of various diseases, such as tumors, strokes, heart problems, and spine disease. A high-quality scan is important for maximizing diagnostic sensitivity and making the right diagnosis. Generally, a high quality image requires high signal to noise ratio (SNR), high contrast to noise ratio (CNR) between normal and pathological tissues, low levels of artifact, and reasonable and acceptable spatial-temporal resolution.

Before the commencement of each magnetic resonance spectroscopy (MRS) or MRI scan, it is common practice to adjust the strength of the transmit field and/or the receiver sensitivity to ensure that the RF excitation and reception have the optimal frequency, strength and duration to evoke the desired MRS or MRI signals. This does not necessarily mean that the expected RF transmit field will be produced uniformly throughout a cross section and/or a volume of the object being imaged, or that the resulting MRS or MRI signals will be received uniformly from all locations. Transmit RF field produced by most transmit coils as loaded by the object being imaged is not homogeneous, and the receiver sensitivity of most receiver coils is similarly not homogeneous. This is particularly true of imperfect coil configuration, such as surface coil and phase array coils. Even if the transmit and receiver coil fields are homogeneous for free space (i.e., the unloaded space or space in the absence of the object), wave behavior and penetration of the RF field into the subject may give rise to non-uniform transmit field and receiver sensitivity throughout the region of interest. This is known as the subject loading effect, and this effect becomes pronounced at higher static $B_0$ magnetic fields such as at static magnetic field of about 3.0 Tesla or higher. Even at lower static magnetic fields, the subject loading effect may be non-negligible. Moreover, the incorrect calibration of the RF pulse amplitude, instability or drift of the RF amplifier or other RF electronics, can lead to non-uniform transmit field. Also, mutual inductance between a transmit coil and a receiver coil may cause further inhomogeneities in the transmit and receive fields.

In order to obtain a detectable MRS or MRI signal, the object being imaged (also referred to herein as "object" or "subject") must be exposed to a static basic magnetic field (usually known as the $B_0$ field) which is as homogeneous as possible. While the magnetic resonance images are being recorded, the basic magnetic field has fast-switched gradient fields superimposed on it for spatial encoding, which are generated by gradient coils. Moreover, using radio-frequency (RF) antennas, RF pulses near Lamour frequency are radiated into the objected being imaged. RF transmit field of a transmit coil is normally designated as $B_1^+$. Using these RF pulses, the nuclear spins of the atoms in the object being imaged are excited such that the atoms are deflected by a so-called "excitation flip angle" from their equilibrium position parallel to the basic magnetic field $B_0$. The nuclear spins then precess around the direction of the basic magnetic field $B_0$. The magnetic resonance signals generated in this manner are recorded by RF receiver coil. The receiver coil may be either the same coil which was used to generate the RF pulses (i.e., a transceiver coil) or a separate receive-only coil. The magnetic resonance images of the object are generated based on the received magnetic resonance signals. The MRS or MRI signal is picked up by a receiver coil. RF field of a receiver coil is normally designated as $B_1^-$. The acquired measurements are digitized and stored as complex numerical values in a "k-space" data. An associated MR image can be reconstructed from the k-space data, for example, by an inverse 2D or 3D fast Fourier transform (FFT) from raw data, which are collected in the spatial frequency domain (the "k-space"). The k-space data usually includes multiple lines acquired with different phase encoding. Each line is digitized by collecting a number of samples. A set of k-space data is converted to an MR image by means of Fourier transformation. Each image point in the magnetic resonance image is assigned to a small body volume known as a "voxel" and each brightness or intensity value of the images points is linked to the signal amplitude of the magnetic resonance signal received from this voxel.

In order to reach the optimal MRI image quality, tradeoffs among (a) scan time, (b) spatial or temporal resolution and (c) signal-to-noise ratio (SNR), have to be made by the developments and applications of MRI techniques. SNR and contrast-to-noise ratio (CNR) are fundamental metric of quality and performance in MRI. The improvement of SNR and CNR are major challenge in MRI system. The lowest SNR and CNR become the limiting factor in scan time or resolution. RF coils are an essential part of the system, functioning as a transmitter or receiver of RF signal. RF fields generated from the RF coils are one of major factors that determine the SNR and CNR. Understanding and estimation of RF field is important in the design and application of MRI system. For example, one of major drawback of MRI is long scan times compared to other imaging modalities. The long scan time of MR imaging is uncomfortable for patients. Additionally, it introduces the potential for motion-related artifacts (especially in critically ill patients), enhance possibility of repeated scans, and increases cost. Over the last decade, parallel imaging technique is employed in nearly every clinical MRI scan to reduce scan time and enable fast data collection. The acceleration factors can reach two- to threefold in routine clinical practice. The shortened scan time can be used to improve patient compliance (particularly for sick patients), to enhance the spatial resolution or increase the volumetric coverage, and reduce the cost of MRI exams.

The quality of images acquired with parallel imaging techniques, including parallel transmit and parallel receive, strongly rely on the transmit field of a transmit coil and the receiver sensitivity of a receiver coil. The accurate estimation of the transmit field and the receiver sensitivity directly influence the performance of the parallel imaging techniques.

The complex transmit field $B_1^+$ of RF transmit coils, including magnitude and absolute phase of transmit field $B_1^+$, is important for many aspects of MRI scanning.

The spatial information of complex transmit field $B_1^+$ of RF transmit coils is important for the following applications such as: (1) coil design and RF safety; (2) transmit shimming and/or parallel transmit; and (3) inhomogeneity correction; (4) quantitative MRI or MRS; (5) simultaneous multi-slice imaging; and (6) exploration of new contrast and biomarker, such as in vivo conductivity. Since the electric conductivity and the regional specific absorption ratio (SAR) depend on the frequency of the applied RF field, we can calculate the electric conductivity and the regional SAR via the absolute phase of transmit field. SAR is a major safety concern in high-field RF coil designs and MRI exams. The transmit field generated by each coil or element includes both magnitude and phase. The absolute phase of the complex transmit field of the coil or element is important input for transmit shimming and/or parallel transmit so that we can adjust the currents of each coil or element create uniform transmit field. The non-uniform transmit field leads to not only signal intensity inhomogeneity but also contrast inhomogeneity because both signal intensity and contrast associate with the flip angles generated by the transmit field. The inhomogeneity of both signal intensity and contrast strongly influence visual and quantitative analyses of MR images. Both RF shimming and parallel transmit have been developed to correct the inhomogeneity. The electric property is estimated by absolute phase of transmit field $B_1^+$.

U.S. Pat. No. 9,229,074 B2 to Tobias Ratko Voigt et al. disclosed that local specific SAR was based on an electric property and the mass density of a segmented geometry of an object. In Phys. Med. Biol. 1991; 36:723-734, Haacke et al. discloses that EPT was estimated by quantitative MRI method. In Magn. Reson. Med. 2011; 66:456-466, Voigt T et al. discloses a method for quantitative conductivity and permittivity imaging of the human brain using EPT. Finally, the absolute phase of transmit field can be used to estimate the conductivity by Maxwell's equations. The accuracy and precision of absolute phase of transmit coil directly relate with those of the estimated conductivity. Therefore, the estimation of complex transmit field is very important for MRI techniques and their applications.

Various methods have been developed to estimate the magnitude of transmit field $B_1^+$. However, the estimation of its absolute phase of transmit field has been unsolved problem for a decade. Any few methods in image domain have been developed to approximately estimate the absolute phase of a transceiver coil and a multiple transmit coils. Most recently, the absolute phase of a transceiver coil can be estimated using multiple sequences and the superposition principle of electromagnetic field. These methods mentioned above estimate absolute phase of the complex transmit field of a transmit coil through approximation methods or existing coil (such as volume coil, virtual coil or one coil element of coil array) as a reference coil. These methods introduce a big error in the estimation of the absolute phase. So far it is not general method to estimate the absolute phase of the transmit field of a transmit coil accurately.

Estimating complex (e.g., absolute phase and magnitude) RF field (or RF receiver sensitivity) $B_1^-$ of a receiver coil is important for various stages of the MRI procedure: (1) coil design; (2) parallel transmit; (3) parallel image reconstruction including magnitude image and/or phase image; (4) the combination of MRI or MRS signals from each element of multiple receivers; (5) exploration of new contrast and biomarker, such as susceptibility-weighted imaging, susceptibility tensor imaging, in vivo conductivity; (6) quantitative MRI and MRS, such as quantitative susceptibility mapping (QSM), temperature and encode flow velocity.

The major two challenge for estimating the complex $B_1^-$ of a receiver coil are (1) that the complex $B_1^-$ should be determined in vivo because the various characteristic of subject being images strongly influence the accuracy of complex $B_1^-$; and (2) other various factors (such as proton density of nuclear spins and transmit field) always entangle with the receiver sensitivity to contribute to the complex MRI or MRS signals. It is very difficult to separate these factors to estimate the complex $B_1^-$ accurately. Various methods have been developed to estimate complex $B_1^-$ from k-space domain, image domain and electromagnetic field. Most methods based on the signal intensity in image domain focus on the estimation of magnitude of the receiver sensitivity. These methods apply a virtual coil or body coil as a reference coil to estimate the coil sensitivity. But the absolute phase of a virtual coil or body coil is not uniform. This greatly creates the big error in estimating the coil sensitivity using the non-uniform absolute phase of the virtual coil or body coil. These methods are not accurate for both magnitude and phase of $B_1^-$ because the effect of in vivo subject being image is ignorable. Additionally, the estimation of complex $B_1^-$ in k-space domain are based on the assumption that the complex $B_1^-$ changes smoothly and slowly, which is mainly determined by the low spatial components frequency of k-space data. Actually, the image contrast of subject being images is determined by the low spatial components frequency of k-space data. Therefore, the low spatial components frequency of k-space data always includes mix information from transmit field, receiver sensitivity and image contrast. It is very difficult to separate these contributions for determining the complex receiver sensitivity. So far the accurate estimation of the complex receiver sensitivity is unsolved problem in MRI and MRS system.

SUMMARY

Described herein is a system and method for estimating the absolute phase of the complex $B_1^+$ of a radiofrequency (RF) transmit coil in an MRI scanner.

In one embodiment, a method for determining spatial distribution of a complex radio frequency (RF) transmit field in a magnetic resonance imaging (MRI) system is provided. The method includes generating a first RF transmit field with a first transmit coil based on imaging parameters, receiving, with a receiver coil, a first set of magnetic resonance (MR) signals from nuclear spins excited by the first RF transmit field, generating a second RF transmit field with a second transmit coil based on the imaging parameters, receiving, with the receiver coil, a second set of MR signals from nuclear spins excited by the second RF transmit field, generating a first set of complex k-space data based on the first set of MR signals, generating a second set of complex k-space data based on the second set of MR signals, and estimating an absolute phase of the first RF transmit field of the first transmit coil based on the first set of complex k-space data and the second set of complex k-space data, and estimating a magnitude of the first RF transmit field of the first transmit coil based on at least another set of complex k-space data acquired with the first transmit coil.

Compared with conventional techniques for approximately estimating the absolute phase of transmit field $B_1^+$ using magnitude or phase images, the techniques described herein greatly improve the accuracy of the absolute phase of transmit field $B_1^+$ mapping through configuring and/or adjusting (shimming) the current phase distribution of a reference transmit coil to obtain the uniform absolute phase of the reference transmit coil as a reference phase. It should be understood that the techniques described herein can be applied in a wide range of applications including, but not limited to, RF transmit coil design, parallel transmit imaging, RF shimming, simultaneous multi-slice imaging, inhomogeneity transmit correction, RF safety, image quality improvement, complex scanner design, electromagnetic property tomography imaging with MRI, and quantitative MRI/MRS.

In another embodiment, a method for determining a spatial distribution of complex receiver sensitivity of a transceiver coil in a magnetic resonance imaging (MRI) system is provided. The method includes generating a RF transmit field with a transceiver coil, estimating an absolute phase of the RF transmit field of the transceiver coil, estimating a magnitude of the RF transmit field of the transceiver coil, receiving a set of complex k-space data based on a set of MR signals from nuclear spins excited and received by the transceiver coil, estimating an absolute phase of a receiver sensitivity of the transceiver coil based on a phase image reconstructed from the set of complex k-space data and the absolute phase of the RF transmit field, and estimating a magnitude of the receiver sensitivity of the transceiver coil based on the magnitude of the RF transmit field, the absolute phase of the RF transmit field, and the absolute phase of the receiver sensitivity.

Compared with conventional techniques for approximately estimating complex $B_1^-$ from the signal intensity from a virtual or reference receiver coil, the techniques described herein directly estimate complex $B_1^-$ of the transceiver coil as a receiver and complex $B_1^+$ of the transceiver coil as a transmitter. This disclosure greatly improves the accuracy of complex $B_1^-$ mapping. It should be understood that the techniques described herein can be applied in a wide range of applications including, but not limited to, RF receiver coil design, parallel imaging, image combination, inhomogeneity receiver correction, image quality improvement, complex scanner design, electromagnetic property tomography imaging with MRI, and quantitative MRI/MRS.

In yet another embodiment, a magnetic resonance imaging (MRI) system for determining spatial distribution of the complex receiver sensitivity of a transceiver coil in a magnetic resonance imaging (MRI) system is provided. The MRI system includes a transceiver coil; a processing unit; a system memory, and machine readable instructions stored in the system memory that, when executed by the processing unit, cause the MRI system to: generate a RF transmit field with the transceiver coil; estimate an absolute phase of the RF transmit field of the transceiver coil; estimate a magnitude of the RF transmit field of the transceiver coil; generate a set of complex k-space data based on a set of MR signals from nuclear spins excited by the RF transmit field; estimate an absolute phase of a receiver sensitivity of the transceiver coil based on a phase image reconstructed from the set of complex k-space data and the absolute phase of the RF transmit field; and estimate a magnitude of the receiver sensitivity of the transceiver coil based on the magnitude of the RF transmit field, the absolute phase of the RF transmit field, and the absolute phase of the receiver sensitivity.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
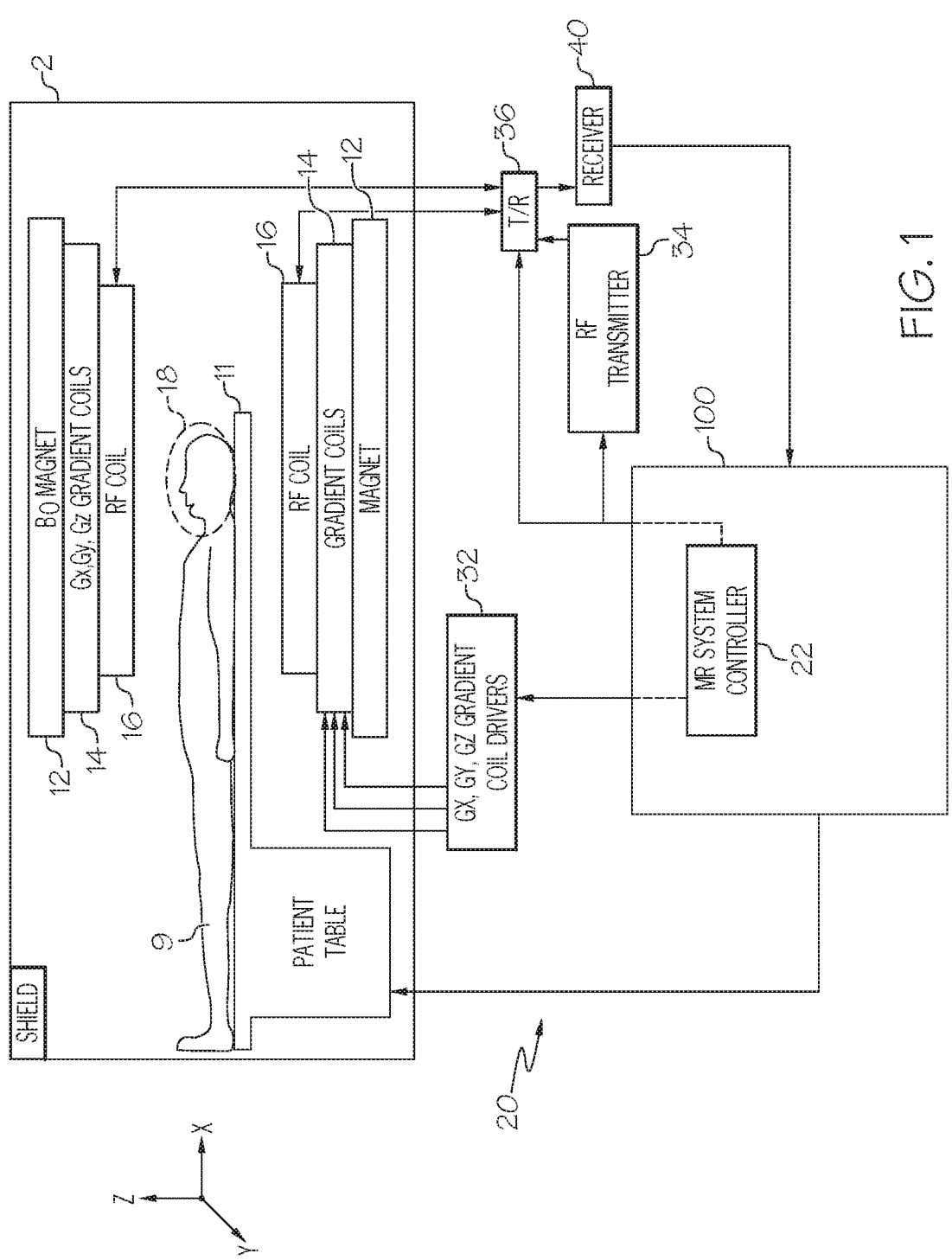
FIG. 1 is a diagram illustrating an example MRI system.

Unless defined otherwise, all technical and scientific terms used herein have the same meaning as commonly understood by one of ordinary skill in the art.

Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not.

Definitions

Volume coils (e.g., the body coil) completely encompass the region of interest being imaged and can be operated as transmit coils, or receiver coils, or both.

A transceiver coil is a RF coil which is used for both transmission and reception without any configuration change.

$B_{1t}$ is the transmit RF field which is generated by a transmit coil in MRI system. $B_{1t}$ includes a transversal transmit field (e.g. $B_{xt}$ along x-axis and $B_{yt}$ along y-axis) and a longitudinal transmit field $B_{zt}$ along z-axis.

$B_{1r}$ is the receiver RF field which is generated by a receiver coil in MRI system. $B_{1r}$ includes a transversal receiver field (e.g. $B_{xr}$ along x-axis and $B_{yr}$ along y-axis) and a longitudinal receiver field $B_{zr}$ along z-axis.

$B_1^+$ the positive circularly polarized component of a transversal transmit field of a RF pulse which is generated by a transmit coil. The RF pulse may be used as an excitation RF pulse, refocused RF pulse, and magnetization preparation RF pulse. The transmit coil may be at least one of volume coil, surface coil, one element of an array coils and their combination. The transversal transmit RF field could be decomposed into two rotating fields: the positive circularly polarized component $B_1^+$ which rotates in the direction of nuclear magnetic moment precession (counterclockwise direction). In MRI system, only the positive circularly polarized component of the transmitting field $B_1^+$ contributes to the excitation of proton nuclei spins. Therefore, as used herein, $B_1^+$ refers to the transmit field of a transmit coil.

$B_1^-$ is the negative circularly polarized component of a transversal receiver field of a receiver coil. Similar to $B_1^+$, the transversal receiver field may be decomposed into two rotating fields: the positive circularly polarized component $B_1^+$ which rotates in the direction of nuclear magnetic moment precession (counterclockwise direction), and the negative circularly polarized component $B_1^-$, which rotates opposite to the direction of precession (clockwise direction). In MRI system, the receiver sensitivity of proton nuclei spins is proportional to the negative circularly polarized component of the transmitting field $B_1^-$. Therefore, as used herein, $B_1^-$ refers to the receiver sensitivity of a receiver coil.

$B_1$ field mapping includes both transmit field mapping or $B_1^+$ mapping of a transmit coil and receiver sensitivity mapping or $B_1^-$ mapping of a receiver coil. It should be understood that the MRI systems described herein may include a plurality of transmit coils and/or a plurality of receiver coils. Optionally, the transmit coils or receiver coils may be an array coil (e.g., transmit coil elements arranged in an array or receiver coil elements arranged in an array). In some implementations, the transmit coils and receiver coils are different coils. In other implementations, the transmit coil and the receiver coil are the same coil (e.g., a transceiver coil). Alternatively or additionally, the transmit coil may include, but is not limited to, a transmit volume coil, a transmit surface coil, or an array coil. The complex $B_1^+$ map described herein can be a complex $B_1^+$ map of a portion of, or the entire of transmit coil or element of an array coil. Alternatively or additionally, the receiver coil may include, but is not limited to, a receiver coil or an array coil. The complex $B_1^-$ map described herein may be a complex $B_1^-$ map of a portion of, or the entire of receiver coil or element of an array coil.

An absolute phase of a transmit field $B_1^+$ of a transmit coil is defined as a phase of the transmit field $B_1^+$ at the zero point of time, which is relative to the phase independent of spatial location.

An absolute phase of receive field $B_1^-$ of a receiver coil is defined as a phase of the receive field $B_1^-$ at the zero point of time, which is relative to the phase independent of spatial location.

RF Field Mapping Overview

RF field mapping includes the estimation of both complex transmit field $B_1^+$ and receiver sensitivity $B_1^-$ which is significant to MRI procedures and applications including, but not limited to, image quality improvement, RF safety, RF coil design and optimization, quantitative MRI, RF shimming, tailored RF shimming, parallel transmit field, image reconstruction, signal combination from each elements, and electromagnetic property tomography.

Either inhomogeneous transmit or inhomogeneous receiver sensitivity or both can gives rise to signal and contrast inhomogeneities in the reconstructed images. Without removing or sufficiently reducing these $B_1$ inhomogeneities, the value of MRI images in clinic and research may be compromised.

The Complex Transmit Field $B_1^+$

The estimation of complex transmit field $B_1^+$ is important for RF safety in high field and ultra-high field MRI. $B_1^+$ inhomogeneities generate a local exposure where most of the absorbed energy is applied to one body region rather than the entire body. As a result, the hotspots may occur in the exposed tissues and may lead to regional damage of these tissues even when global specific absorption rate (SAR) is less than US Food and Drug Administration (FDA) and International Electrotechnical Commission (IEC) SAR limits.

The estimation of complex transmit field $B_1^+$ is important for RF coil design. (a) The uniformity of $B_1^+$ field is important metric for RF coil design and optimization. The $B_1^+$ field estimation is direct and efficient method to evaluate the performance of RF coil. (b) As for a RF coil design and validation, fast and accurate $B_1$ field estimation can improve the efficiency for RF coil design and evaluation. (c) As for specific application RF coil, such as knee coil, breast coil, the RF inhomogeneity can be greatly improved if the loaded effect is taken account into the coil design.

Among signal intensity-sensitive methods for estimating $B_1^+$, there are a couple of double or multi-angle techniques. These methods use multiple (e.g., two) spin- or gradient-echo recalled acquisitions with different flip angles of the exciting RF pulses in the individual sub-experiments. By using the ratio of signal intensities, in case of two acquisitions, or fitting the signal behavior, one can estimate the effective flip angle, which is proportional to the actual $B_1^+$. However, these methods are not efficient, because a long repetition time (TR) need to be used to achieve full relaxation so that the effect of $T_1$ relaxation could be removed. To overcome this limitation magnetization prepared methods have been proposed transferring the double/multi-angle idea into an appropriate preparation of the longitudinal magnetization. This allows a more efficient read out of multiple echoes to reduce the total mapping time. In another technique, the flip angle is calculated from the ratio of a spin echo and a stimulated echo, similar to the double angle methods but with both echoes obtained during the same sequence repetition. In contrast, the actual flip angle technique interleaves two or multiple steady state sequences with significantly differing sequence repetition times (TR).

This phase-sensitive method for estimating $B_1^+$ allows imaging over a much wider range of flip angles than double-angle methods. Another phase sensitive approach, recently introduced, is based on the Bloch-Siegert shift, a physical effect known already for a long time. This is an elegant approach of $B_1^+$ related signal phase encoding. After generating transverse magnetization, a second RF pulse of defined duration and shape is applied off-resonant (several kHz) changing the effective precession field for the transverse magnetization, encoding in this way the magnitude of the $|B_1^+|$ into the MR signal phase. To compensate for other MR intrinsic phase variations, this experiment is repeated without the second RF pulse (or even better with the second RF applied at the off-resonance frequency mirrored to the Lamor frequency). This results in a rather robust approach that is independent of TR, $T_1$ relaxation, flip angle, chemical shift, background field inhomogeneity, and so on. The magnetization thus generated can be read out using a number of MR imaging schemes.

In Magnetic resonance in medicine 2017; 77:1201-1207, Uecker, M et al. discloses a virtual conjugate coil method to determine the background phase accurately and robustly according to conjugate symmetry in k-space. Although the virtual coil is very useful for phase-constrained image reconstruction, the estimated phase is not the absolute phase, but background phase. In most cases, the background phase is completely different from the absolute phase of receiver coil or array coils. Thus, replacing the absolute phase with background phase in MRI system may introduce a significant error.

In IEEE Trans. Med. Imag., 2009; volume 28: p 1365-1374, Katscher et al. discloses a transceiver phase assumption that the absolute transmit phase of a quadrature volume coil was a half of the transceiver phase. The disclosure is only directed to a transceiver coil.

U.S. Patent Application Publication No. 2014/0300354 to He et al. discloses a method for an absolute phase distribution from the derived $B_1^+$ magnitude maps and $B_1^+$ relative phase maps; and a $B_1^-$ absolute phase distribution from the derived $B_1^-$ magnitude maps and $B_1^-$ relative phase maps.

U.S. Patent Application Publication No. 2016/0054262 to Sodickson et al. discloses an approximation method (e.g. a Local Maxwell Tomography approach) to estimate the absolute phase using multiple coil system.

WO 2016/183572 A1 to Jinghua Wang and Yu Ding discloses a system and method for estimating complex transmit field $B_1^+$ of a transmit coil of an MRI system in both k-space and image domains through encoding complex information of the transmit field into the different sequences.

WO 2018/136705 A1 to Jinghua Wang and Yu Ding discloses a system and method for estimating complex transmit field $B_1^+$ of a transmit coil of an MRI system using the phase images acquired with the different coil configurations.

The inventions and literatures mentioned above estimate absolute phase of the complex transmit field of a transmit coil through approximation methods or existing coil as a reference coil. For example, it is assumed that the absolute phase of transmit field equals to the absolute phase of receiver sensitivity in birdcage coil or volume coil to estimate the absolute phases. Additionally, a virtual coil or a coil element is used as a reference coil to calculate the absolute phase of the other coil. Generally, the absolute phase of virtual coil or a coil element is not uniform and is not ignorable.

The present method for the absolute phase of the transmit field is determined through the comparison of two phase images acquired with the transmit coil and a reference transmit. The reference coil is configured or adjusted to minimize its absolute phase. Additionally, it is assumed that the minimal absolute phase of transmit field of the reference transmit coil is ignorable and approximated to be zero, compared with the absolute phase of the target transmit coil, particularly for a birdcage or volume coil as a target transmit coil. As a result, the accuracy of estimating absolute phase of the complex transmit field of a transmit coil is greatly improved.

Correction of $B_1^+$ inhomogeneity is important for quantitative MRI, such as quantitative fast $T_1$ mapping and MR image segmentation. It is known that contrast-to-noise ratio and signal inhomogeneity are major reasons which strong affect the performance of segmentation. In quantitative MRI, one solution is to measure $B_1^-$ maps and correct the intensity inhomogeneities that arise from $B_1^-$ variations.

Both transmit field $B_1^+$ and receiver sensitivity $B_1^-$ mapping may provide the information about coil performance and inhomogeneity and be used for preventive maintenance of RF system, including transmit coil and/or receiver coil system.

Complex Receiver Sensitivity

SENsitivity Encoding (SENSE) is a parallel imaging technique which unfolds superimposed pixels in the image domain. The receiver sensitivity of each coil is needed for SENSE reconstruction directly. The receiver sensitivity of each coil is typically measured by a prescan with a low spatial resolution. Additionally, the receiver sensitivity of each coil may be lowpass filtered or fitted to a polynomial model to reduce noise.

GeneRalized Partially Parallel Acquisitions (GRAPPA) synthesizes missing data points directly in k-space. GRAPPA applies correlation of each coil to reconstruct missing k-space data using neighboring acquired points. It does not require the receiver sensitivity of each coil directly, but it requires only implicit receiver sensitivity. When the images obtained from GRAPPA, the receiver sensitivity of each coil can be used for combining the images acquired from each coil into one image.

Parallel imaging techniques rely on the linear superposition of the electromagnetic fields produced by the individual coils or coil elements of the MRI system. For most applications, the distribution of RF field produced by each coil or element must be known in magnitude and phase at least relatively to that of the other channels. For example, signals of magnetic resonance image (MRI) and magnetic resonance spectroscopy (MRS) from multiple receiver coils can be combined to maximize the signal-to-noise ratio (SNR) using known receiver sensitivity and noise covariance. The Biot-Savart law or phantom replacement has been used to estimate complex receiver sensitivity for coil combination, saturation correction, or sensitivity correction. But, these approaches are awkward and inaccurate for coil combination in vivo.

Generally, acceleration factors of 2 or 3 are applied during clinical routine scans. Higher acceleration factors are not reached because of two factors: first, the signal-to-noise ratio (SNR) is reduced by the square root of the acceleration factor because of the reduced amount of k-space samples. Secondly, noise is amplified during the image reconstruction process. Noise amplification originates from image reconstruction process as an inverse problem. But noise amplification can be reduced by applying phase-constrained parallel MRI algorithms. In these algorithms, phase distribution information, even relative phase information, directly influences the reconstruction quality. In other words, both phase and magnitude of RF receiver sensitivity $B_1^-$ contribute to the image quality of phase-constrained parallel MRI methods.

Additionally, parallel transmit technique is coil configuration, object and sequence dependent. Therefore, the receiver sensitivity $B_1^-$ must be estimated for each coil, object and sequence in parallel transmit technique. Reducing time for estimating receiver sensitivity $B_1^-$ will reduce the time of applying parallel transmit technique in clinical setting. The estimation of receiver sensitivity $B_{1,r}^-$ is precondition of parallel transit techniques.

$B_1^-$ mapping has an increasing role in electrical property tomography. The conductivity and permittivity of living issues can be directly estimated using $B_1^-$ mapping. For example, Hancu et al. proposes a method in which the complex phase of a specific image is proportional to the product of the transmit radio frequency magnetic field and the receive RF magnetic field for a transceiver coil to simplify the symmetry assumption of transceiver phase.

Recently, three major developments can be envisaged in an MRI: the use of parallel acquisition methods, the move to high field, and the development of new scanner designs such as open access scanners. For these developments, the inhomogeneous signal intensity from non-tissue characteristics (inhomogeneous transmission and reception) has been being a greater problem. Estimating transmit field and receiver sensitivity is precondition of developing the techniques to correct the inhomogeneous signal intensity which is caused by the transmit field and receiver sensitivity.

The receiver sensitivity $B_1^-$ of a receiver coil may be mapped directly by MRI techniques in both k-space domain and image domain. Here, it is noted that transmit coils may be different from receiver coils.

Various in vitro and in vivo methods have been proposed to estimate receiver sensitivity $B_1^-$. The in vitro methods include the simulation method and phantom pre-scan method. The simulation method estimates the receiver sensitivity based on the configuration of the receiver coil and the electromagnetic properties of the loaded object. It is time consuming and not accurate. The phantom pre-scan method assumes that the receiver sensitivity of the loaded condition is identical to that of a uniform phantom. The method is apparently not accurate. Generally, receiver sensitivity depends on both coil configuration and properties of the loaded object.

The in vivo methods intensity-based methods, field-based methods, and k-space calibration methods for estimating receiver sensitivity $B_1^-$. The intensity-based methods include the pre-scan method, the minimal contrast method, and the uniform magnetization method. In the pre-scan method, the sensitivity distributions of the respective RF receiving coils are calculated based on the assumption that the body coil has a relatively uniform sensitivity distribution, which is however only approximately true at low field strengths when the wave behavior and RF penetration of the RF magnetic field can be ignored. When the field strength is high, the assumption is no longer valid. Moreover, sometimes an MRI system may not have any body coil or volume coil, in which case the pre-scan method is not used to estimate receiver sensitivity. The minimal contrast image method and uniform magnetization method can estimate receiver sensitivity in vivo and greatly improve the accuracy of receiver sensitivity estimation. But these methods are limited in their practical applications, particularly in configurations involving multiple tissue types.

In Magnetic Resonance in Medicine, 2002; 47:529-538, McKenzie, C. A., et al. discloses a self-calibrating method for complex coil sensitivity. The phase information of receiver sensitivity is also extracted by auto-calibration in parallel MRI reconstructions. The calibration method implements fully sampled central k-space lines to determine the complex coil sensitivity. But the central k-space includes all low-spatial-frequency components including transmit field, object being imaged, and coil sensitivity. This method therefore assumes that the contribution from other factors to central k-space is ignorable and coil sensitivity is dominant. The assumption is not available in most cases.

U.S. Pat. No. 6,559,642 B2 to Kevin F King Sheng discloses a method to estimate the coil sensitivity matrix of each local coil in a coil array by a sensitivity encoded MRI pre-scan. The coil sensitivity of each local coil is obtained by taking the ratio of the complex calibration images acquired with the body coil and each of the surface coils. That is, the body coil is used as a reference coil for estimating coil sensitivity of each surface coil.

WO 2003/060528 A3 and U.S. Pat. No. 6,697,661 B2 to Raghu Raghavan et al. disclose a method to calibrate the coil sensitivity of a movable receiver coil in a magnetic resonance imaging environment using an inserted microcoils. Microcoils' electrical properties (inductance, capacitance, etc.) in a tissue are different from coils' electrical properties in vacuum. The coil sensitivity is calculated by the interaction among receiver coil, microcoils and tissues. The methods is time-consuming and in accurate. (electromagnetic field method)

WO 2002/056767A1 and U.S. Pat. No. 6,949,928 B2 to Miguel Angel Gonzalez Ballester and Yoshio Machida disclose a method to estimate the coil sensitivity of a multicoil composed of a plurality of coil elements by fitting global coverage splines to the initial sensitivity map[42]. The initial sensitivity map is estimated using a body coil as a reference coil. The global coverage splines are used to refine the estimation of coil sensitivity.

WO2003/096046A1 and U.S. Patent Application Publication No. 2005/0200357 A1 to Klaas Paul Pruessmann et al. disclose a method for fast magnetic resonance imaging using receiver coil sensitivity[43]. Sensitivity map is created from a conventional reference scan. The contributions in individual positions of the receiver coil images from different positions in the image are disentangled from the receiver coil images and the sensitivity profiles.

U.S. Pat. No. 7,064,547 B1 to Kevin F. King et al. disclosed a method for fast MR imaging with the acquisition of coil sensitivity calibration data which was performed with a low resolution image data. That is, the calibration FOV is different from the image FOV.

U.S. Pat. No. 7,187,791 B2 to Yoshikazu Ikezaki discloses a method to estimate the coil sensitivity of phase array coils by the two-dimensional curve fitting. The initial coil sensitivity of each coil element or coil array is estimated by taking the ratio of the virtual image and image acquired with the coil element. The virtual image is calculated by the sum of absolute value of images acquired with the coil element.

WO 2005/071429 A1 and U.S. Patent Application Publication No. 2007/0182410 A1 to Anne Niemi et al. disclose a method to estimate the coil sensitivity profiles of the coils from image data of a calibration scan which is performed using either a spin echo type sequence for each calibration or a gradient recalled echo sequence with a short echo time for each calibration to reduce the effect of read-out gradient.

U.S. Pat. No. 7,254,435 B2 to Qiang Zhang et al. discloses a method to estimate the coil sensitivity calibration for the respective coils from k-space data acquired in the reference lines. That is, coil sensitivity calibration is estimated in the k-space domain. When the sequence and transmit coil used for imaging scan are different from those in calibration scan, the reconstructed imaging from the coil sensitivity calibration and imaging data might have a big artifact.

U.S. Pat. No. 7,492,153 B2 to Anja C. S. Brau et al. discloses a method to estimate the coil sensitivity map of a plurality of RF source coils (SENSE) or calibrate the receiver coil sensitivity variation (GRAPPA) based on the relationship between the autocalibration MR data from each of the plurality of RF source coils and the low resolution MR data from the RF target coil. That is, the RF target coil is used as a reference coil to estimation the coil sensitivity or its variation.

U.S. Pat. No. 7,375,523 B1 to Ileana Hancu discloses a system and method for estimating the coil sensitivity using a neural network or other computer intelligence method from sample MR data normalizations. The method separates the contribution of transmit field and receiver sensitivity to MR signal. However, complexity of object being imaged increases the time to obtain the receiver sensitivity and reduce its accuracy.

WO 2007/121023A1 and U.S. Patent Application Publication No. 2009/0278536 A1 to Richard Winkelmann and Peter Boernert disclose a method to estimate the receives sensitivity maps of each of a plurality of parallel imaging coil elements by taking the ratio of signal intensity of images acquired with each coil element and whole-body coil. The pixel or voxel with low SNR signal of image acquired with body coil as a receiver is refined using a wave propagation model. The whole body coil is used as a reference coil to estimate the receiver sensitivity.

U.S. Pat. No. 7,777,487 B2 to Lei Ying and Jinhua Sheng discloses a method to improve the accuracy of estimating the coil sensitivities using the subsampled data from outer k-space and auto-calibration center k-space data.

U.S. Pat. No. 8,076,938 B2 to Anja C. S. Brau and Philip James Beatty discloses a method to improve the accuracy of the coil sensitivities using a virtual coil which was generated based from the plurality of RF source coils. That is, the virtual coil is used as a reference receiver coil to estimate the coil sensitivity.

WO 2012/001583 A1 and U.S. Patent Application Publication No. 2013/0099786 A1 to Feng Huang et al. disclose a method to estimate the coil sensitivity using the image data from the set of coil array and the body coil. The body coil is used as a reference receiver coil to estimate the coil sensitivity.

U.S. Pat. No. 8,093,894 B2 to Yoshio Machida and Nobuyasu Ichinose disclose a method to estimate the coil sensitivity using a reference image which is acquired with whole body coil or is generated by images acquired with phased array coils. Furthermore, a correction processing is used to reduce the effect of non-uniform reference image on the accuracy of the coil sensitivity. This method also applies a reference image to estimate the coil sensitivity.

U.S. Pat. No. 8,334,694 B2 to Ek Tsoon Tan and Stephen J Riederer discloses a method to estimate the coil sensitivities of a plurality of coils using inversion recovery pulse sequence[53].

U.S. Pat. No. 8,379,951 B2 to Michael Lustig and John M. Pauly discloses a method to calibrate parallel imaging reconstruction from data points of each data set.

U.S. Patent Application Publication No. 2014/0088899 A1 to Jun Liu et al. discloses a method to estimate the coil sensitivities with the auto-calibrated coil-by-coil reconstruction.

U.S. Pat. No. 9,316,707 B2 to Mohammad Mehdi Khalighi and Brian Rutt discloses a method to estimate the coil sensitivities with the $B_1^+$ field map and the proton density weighted image.

U.S. Pat. No. 9,759,786 B2 to Yusuke Asaba et al. discloses a method to estimate the coil sensitivities of a coil device having n coil modes using the data from the first scan with the selected coil mode.

The inventions and literatures mentioned above estimated the complex receiver sensitivity through the signal intensity or k-space calibration of a virtual coil or a reference coil with a reference scan.

The field-based methods include the reciprocity principle method, the rotating-object method, and calibration based on transmit field. At low field strengths, the difference between the transmit field and receiver sensitivity for a transceiver coil is small and can be ignored because the phase is constant inside an object. The reciprocity principle works very well. In that case, quasi-static approximation (Biot-Savart's Law) can depict the transmission and reception fields very well. Thus, receiver sensitivity can be replaced with the transmit field at low field strengths for transceiver coils. Various methods have been proposed for estimating transmit fields in vivo. These methods can be categorized into MR amplitude based and MR phase based methods. MR amplitude based methods include double flip angle method, dual pulse spin echo, actual flip angle imaging, and stead state method. MR phase based methods include Bloch Siegert shift method, and phase method. However, the wavelength of the RF magnetic field in high fields becomes less than $\frac{1}{10}$ of the size of the object. The phase distribution of the magnetic field inside the object must then be considered. The difference between the transmit field and receiver sensitivity becomes significant at high field strengths and the reciprocity principle no longer works. Replacing receiver sensitivity with transmit field will introduce significant errors in quantitative MRI and large artifacts in parallel imaging reconstruction.

The measured transmit field is a left-handed circularly-polarized component of a transceiver coil as a transit coil. When the relative direction between equilibrium magnetization and the main magnetic field is reversed by either rotating the object or inverting the main magnetic field, the measured pseudo-transmit field $B_1^+$ is a right-handed circularly polarized component of the coil before rotating the object or inverting the field. The right-handed field component is the receiver sensitivity $B_1^-$ of the transceiver coil as a receiver coil. It is noted that a right-handed circularly-polarized component of a transceiver coil as a transit coil $B_1^-$ is not equal to the right-handed circularly-polarized component $B_1^-$ of the transceiver coil as a receiver coil.

U.S. Pat. No. 9,146,293 B2 to Jinghua Wang et al disclosed three methods (an electromagnetic field method, a bias field method, and a uniform transmit field method) for estimating magnitude of $B_1^-$ of an arbitrary receiver coil. The accuracy of the resulting magnitude of $B_1^-$ can be influenced by the accuracy of estimating the bias field for both the bias field method and the uniform transmit field method. The electromagnetic field method is limited by the difference which is caused by the transceiver coil as a transmit coil and a receiver coil. It is noted that $B_1^-$ of transceiver coil as a transmit coil is not equal to $B_1^-$ of transceiver coil as a receiver. Only if the transceiver coil is single loop coil, $B_1^-$ can equal to BC.

The present method for estimating the complex receiver sensitivity of a receiver coil through a reference of complex receiver sensitivity of a transceiver coil as a receiver coil.

The complex receiver sensitivity $B_1^-$ of a transceiver coil is determined by a pseudo-transition coil that is used to simulate the RF field $B_1^-$ of the transceiver coil as a receiver coil. Additionally, the complex receiver sensitivity $B_1^-$ is estimated based on the transmit field of the transceiver coil and the absolute phases of the transceiver coil as both transmitter and receiver coils.

In vivo methods for estimating $B_1^-$ include intensity-based methods, field-based methods, and k-space calibration methods. The intensity-based methods include the pre-scan method, the minimal contrast method (MCI), and the uniform magnetization method. In the pre-scan method, the sensitivity distributions of the respective RF receiving coils are calculated based on the assumption that the body coil has a relatively uniform sensitivity distribution, which is however only approximately true at low field strengths when the wave behavior and RF penetration of the RF magnetic field can be ignored. When the field strength is high, the assumption is no longer valid. Moreover, sometimes an MRI system may not have any body coil or volume coil. The pre-scan method cannot be used to estimate receiver sensitivity. The minimal contrast image method and uniform magnetization method can estimate receiver sensitivity in vivo and greatly improve the accuracy of receiver sensitivity estimation. But these methods are limited in their practical applications, particularly in configurations involving multiple tissue types.

The field-based methods for estimating $B_1^-$ include the reciprocity principle method, the rotating object method, and calibration based on transmit field. At low field strengths, the difference between the transmit field and receiver sensitivity for a transceiver coil is small and can be ignored because the phase is constant inside an object. The reciprocity principle works well. In that case, quasi-static approximation (Biot-Savart's Law) can depict the transmission and reception fields well. Thus, receiver sensitivity can be replaced with transmit field at low field strengths for transceiver coils.

Coil sensitivity calibration includes auto- or self-calibrating methods. The idea is to record coil sensitivity information directly during the actual scan by adding a small number of additionally acquired fully Fourier-encoded auto-calibration lines. Direct sensitivity calibration for each image is beneficial in combination with flexible coil arrays or for imaging of uncooperative patients. Various auto-calibration methods have also been used to estimate receiver sensitivity for parallel imaging reconstruction because coil sensitivity varies slowly and smoothly over space. The auto-calibration methods also have some drawbacks, although they are good for parallel imaging reconstruction. Receiver sensitivity is a property of the receiver coil, independent of transmit coil, acquisition sequence, and imaging parameters. But receiver sensitivity estimated using the auto-calibration methods depends tremendously on these factors, indicating the inaccuracy of the method. This is because all calibration methods introduce a virtual receiver coil whose receiver sensitivity is equal to the square root of the sum of the squares of receiver sensitivity of each coil element, and assume that the sensitivity of the virtual coil is uniform. In practice, this assumption is problematic, particularly at high field strengths and if the imaged object is of a large size. The errors in estimated receiver sensitivity using auto-calibration methods are not problematic for qualitative parallel image reconstruction because artifacts of reconstruction are dominated by relative receiver sensitivity. However, they are problematic for quantitative parallel image reconstruction or quantitative MRI using internal and external references. In addition, the auto-calibration methods also require additional scan time to obtain additional reference k-space line(s).

U.S. Pat. No. 9,146,293 B2 to Wang et al., entitled "Methods and apparatus for accurate characterization of signal coil receiver sensitivity in magnetic resonance imaging (mri)," describes three methods for estimating in vivo receiver sensitivity. First, the electromagnetic field method is used to estimate the receiver sensitivity of transceiver coils. The method is based on measurements of the transmit field of transceiver coils. The sensitivity of a receive-only coil can be obtained using a reference method with the measured transceiver coil receiver sensitivity. The other two methods, the bias field method and the uniform transmit field method, are based on post-processing of MR signal intensity. The bias field method includes estimations of the transmit field and bias field. Receiver sensitivity is determined using the estimated transmit field and bias field. The uniform transmit field method is realized using either transmit field shimming or adiabatic pulse methods. Because transit fields are assumed to be uniform after applying either transmit field shimming or adiabatic pulses, receiver sensitivity is determined by estimating the bias field of the acquired image using the uniform transmit field.

U.S. Pat. No. 8,502,538 B2 to Dannels et al., entitled "$B_1$ and/or $B_0$ mapping in MRI system using k-space spatial frequency domain filtering with complex pixel by pixel off-resonance phase in the $B_0$ map," describes frequency filtering of spatially modulated or "tagged" MRI data in the spatial frequency k-space domain to estimate $B_1$ and/or $B_0$ maps for an MRI system.

Most of these above mentioned $B_1^-$ mapping methods deal only with either the magnitude or the phase of $B_1^-$ related to a virtual receiver coil or a reference receiver coil. In other words, few of the above mentioned $B_1^-$ mapping methods deal with $B_1^-$ as complex number, that is, both magnitude and phase of $B_1^-$ should be estimated simultaneously. The methods mentioned above for complex $B_1^-$ mapping all deal complex $B_1^-$ mapping with signal intensity. None of them deal complex $B_1^-$ of a transceiver coil with the complex $B_1^+$ of the transceiver coil. For example, the accurate information of complex $B_1^-$ is important for image reconstruction. Compared with existing $B_1^-$ mapping methods, $B_1^-$ mapping techniques described herein provide fast, robust, and accurate complex $B_1^-$.

MRI System Overview

FIG. 1 depicts an MRI system 10, according to one or more embodiments described and shown herewith. In embodiments, the MRI system 10 shown in FIG. 1 includes a patient table 11, a static magnetic field generating unit 12, a gradient magnetic field generating unit 14 for generating respective magnetic fields in proximity to a target area 18 of an object 9, a transmitting and receiving unit 16, and a computing device 100. The patient table 11, the static magnetic field generating unit 12, the gradient magnetic field generating unit 14, and the transmitting and receiving unit 16 are placed within MRI RF shielding area 2 where noise of radio frequency is prevented from entering.

The static magnetic field generating unit 12 includes a main magnet configured to generate a strong static magnetic field in proximity to the target area 18 of the object 9. The static magnetic field generating unit 12 may be arranged to surround the target area 18 of the object 9. For example, the static magnetic field generating unit 12 may be a cylindrical-shaped unit. The gradient magnetic field generating unit 14 includes gradient magnetic field coils for generating gradient magnetic fields in an x-axis direction, a y-axis direction, and a z-axis direction, which are orthogonal to each other. The gradient magnetic field generating unit 14 may be arranged to surround the target area 18 of the object 9. For example, the gradient magnetic field generating unit 14 may be a cylindrical-shaped unit.

In embodiments, the transmitting and receiving unit 16 may include a transmission coil and a receiving coil. The transmission coil irradiates RF pulses to the object 9 and the receiving coil receives MR signals generated by the object 9. In some embodiments, the transmitting and receiving unit 16 may include a transceiver coil having the functions of both the transmission coil and the receiving coil. The receiving coil may be composed of, for example, a so-called array coil in which, for example, a plurality of coil elements are disposed to detect the MR signals generated by the object 9. An RF transmitter 34 may control the transmission coil of the transmitting and receiving unit 16 to irradiate RF pulses. A receiver 40 may receive MR signals generated by the object 9 from the receiving coil of the transmission and receiving unit 16. The RF transmitter 34 and the receiver 40 may communicate with the transmitting and receiving unit 16 through a transmitter/receiver interface 36.

In embodiments, the MRI system 10 includes the computing device 100. The computing device 100 includes a MRI system controller 22. The MRI system controller 22 may control the operations of the gradient coil drivers 32 that activate the gradient coils of the gradient magnetic field generating unit 14. The MRI system controller 22 may also control the operations of the RF transmitter 34 that activates the RF coil of the static magnetic field generating unit 12. The computing device 100 may receive MR signals from the receiving coil of the transmission and receiving unit 16 and reconstruct an MRI image based on the received MR signals. The details of the computing device 100 will be further described with reference to FIG. 1A below.

In embodiment, the computing device 100 may be operably coupled to other components of the MRI system 10, for example, using by any medium that facilitates data exchange between the components of the MRI system 10 and the computing device 100 including, but not limited to, wired, wireless and optical links. For example, the computing device 100 may convert the MR signals received from the transmitting and receiving unit 16 into k-space data. The computing device 100 may generate MR image data from the k-space data with image reconstruction processing. In some embodiments, the techniques for improving image quality with optimal variable flip angles may optionally be implemented using the MRI system 10.

Example Computing Device

Figure 1A:
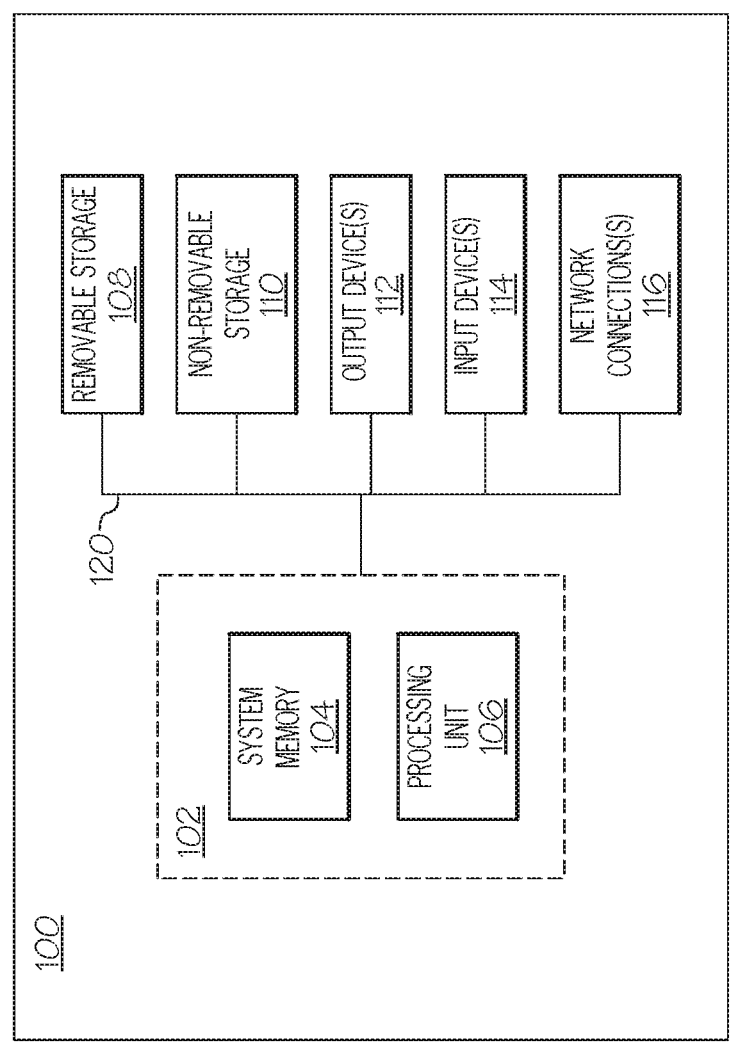
FIG. 1A is an example computing device.

FIG. 1A depicts a computing device 100 according to one or more embodiments shown and described herein. It should be appreciated that the logical operations described herein with respect to the various figures may be implemented (1) as a sequence of computer implemented acts or program modules (i.e., software) running on a computing device (e.g., the computing device described in FIG. 1A), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

It should be understood that the computing device 100 is only one example of a suitable computing environment upon which embodiments of the invention may be implemented. Optionally, the computing device 100 may be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In embodiments, the computing device 100 includes a controller 102 that includes one or more processing units 106 and one or more system memory modules 104. The controller 102 may be the same controller as the MRI system controller 22 in FIG. 1. In other embodiments, the controller 102 may be a separate controller from the MRI system controller 22 in FIG. 1. Depending on the exact configuration and type of computing device, the one or more memory modules 104 may be volatile (such as random access memory (RAM)), non-volatile (such as read-only memory (ROM), flash memory, etc.), or some combination of the two. The one or more processing units 106 may be a standard programmable processor that performs arithmetic and logic operations necessary for operation of the computing device 100.

In embodiments, the computing device 100 includes communication path 120 that provides signal interconnectivity between various components of the computing device 100. Accordingly, the communication path 120 may communicatively couple any number of processing units 106 with one another, and allow the components coupled to the communication path 120 to operate in a distributed computing environment. Specifically, each of the components may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 120 may be formed from any medium that is capable of transmitting a signal such as, for example, conductive wires, conductive traces, optical waveguides, or the like. In some embodiments, the communication path 120 may facilitate the transmission of wireless signals, such as Wi-Fi, Bluetooth, Near Field Communication (NFC) and the like. Moreover, the communication path 120 may be formed from a combination of mediums capable of transmitting signals. In one embodiment, the communication path 120 comprises a combination of conductive traces, conductive wires, connectors, and buses that cooperate to permit the transmission of electrical data signals to components such as processors, memories, sensors, input devices, output devices, and communication devices. Accordingly, the communication path 120 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The one or more processing units 106 may be configured to execute program code encoded in tangible, computer-readable media. Tangible, computer-readable media refers to any media that is capable of providing data that causes the computing device 100 (i.e., a machine) to operate in a particular fashion. Various computer-readable media may be utilized to provide instructions to the one or more processing units 106 for execution. Example tangible, computer-readable media may include, but is not limited to, volatile media, non-volatile media, removable media and non-removable media implemented in any method or technology for storage of information such as computer readable instructions, data structures, program modules or other data. One or more system memory modules 104, a removable storage 108, and a non-removable storage 110 are all examples of tangible, computer storage media. Tangible, computer-readable recording media may include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In embodiments, the one or more processing units 106 may execute program code stored in the one or more system memory modules 104. For example, a bus may carry data to the one or more system memory modules 104, from which the one or more processing units 106 receive and execute instructions. The data received by the one or more system memory modules 104 may be optionally stored on the removable storage 108 or the non-removable storage 110 before or after execution by the processing unit 106.

In embodiments, the computing device 100 may include additional storage such as removable storage 108 and non-removable storage 110 including, but not limited to, magnetic or optical disks or tapes.

The computing device 100 may also have input device(s) 114 such as a keyboard, mouse, touch screen, etc. The input device may be manipulated by an operator to input signals to the MRI apparatus to set the imaging method group, the performing order, the imaging condition, and the like. The computing device 100 may also have output device(s) 112 such as a display, speakers, printer, etc. The output device 112 may output image data such as local image data, diagnosis image data using display, printer and other displayer. The additional devices may be connected to the bus in order to facilitate communication of data among the components of the computing device 100.

Computing device 100 may also contain network connection(s) 116 that allow the device to communicate with other devices. The network connection(s) 116 may be any device capable of transmitting and/or receiving data via a wireless network. Accordingly, the network connection(s) 116 may include a communication transceiver for sending and/or receiving data according to any wireless communication standard. For example, the network connection(s) 116 may include a chipset (e.g., antenna, processors, machine readable instructions, etc.) to communicate over wireless computer networks such as, for example, wireless fidelity (Wi-Fi), WiMax, Bluetooth, IrDA, Wireless USB, Z-Wave, ZigBee, or the like.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

In some embodiments, the computing device 100 may include a workflow setting unit, an imaging operation determining unit, and an image reconstruction unit. The workflow setting unit may be a program module stored in the system memory modules 104. The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by the input unit is minimized. The imaging operation determining unit determines whether an imaging operation during a main imaging is implemented according to the workflow. In embodiments, the workflow setting unit and/or the imaging operation unit may be implemented using hardware, software, and or a combination thereof.

The image reconstruction unit may include an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

Methods and Results

Estimating Complex Transmit Field $B_1^+$ of a Transmit Coil

Various factors, such as transmit coil configuration, uncompensated eddy currents, wave behavior and object positioning, generate inhomogeneous transmit field. The nominal flip angle of α is defined by averaged flip angles cross volume being imaged. Thus, the actual flip angle should be a function of location. The goal of $B_1^+$ mapping is to estimate the function of flip angle as a space distribution. In most MRI applications, only magnitude images are used.

A number of techniques have been proposed for estimating magnitude of transmit field $B_1^+$ in vivo in both image domain and k-space domain. However, the estimation of its absolute phase has been unsolved problem for a decade. The existing method for estimating the absolute phase is based on approximation or a reference coil. For example, it is assumed that the transmit absolute phase of a birdcage coil or volume coil equals to the receiver absolute phase of the birdcage coil or volume coil in order to estimate absolute phases. Additionally, a virtual coil or a coil element is used as a reference coil to calculate the absolute phase of the other coil. Generally, the absolute phase of a virtual coil or a coil element is not uniform and is not ignorable.

Figure 2:
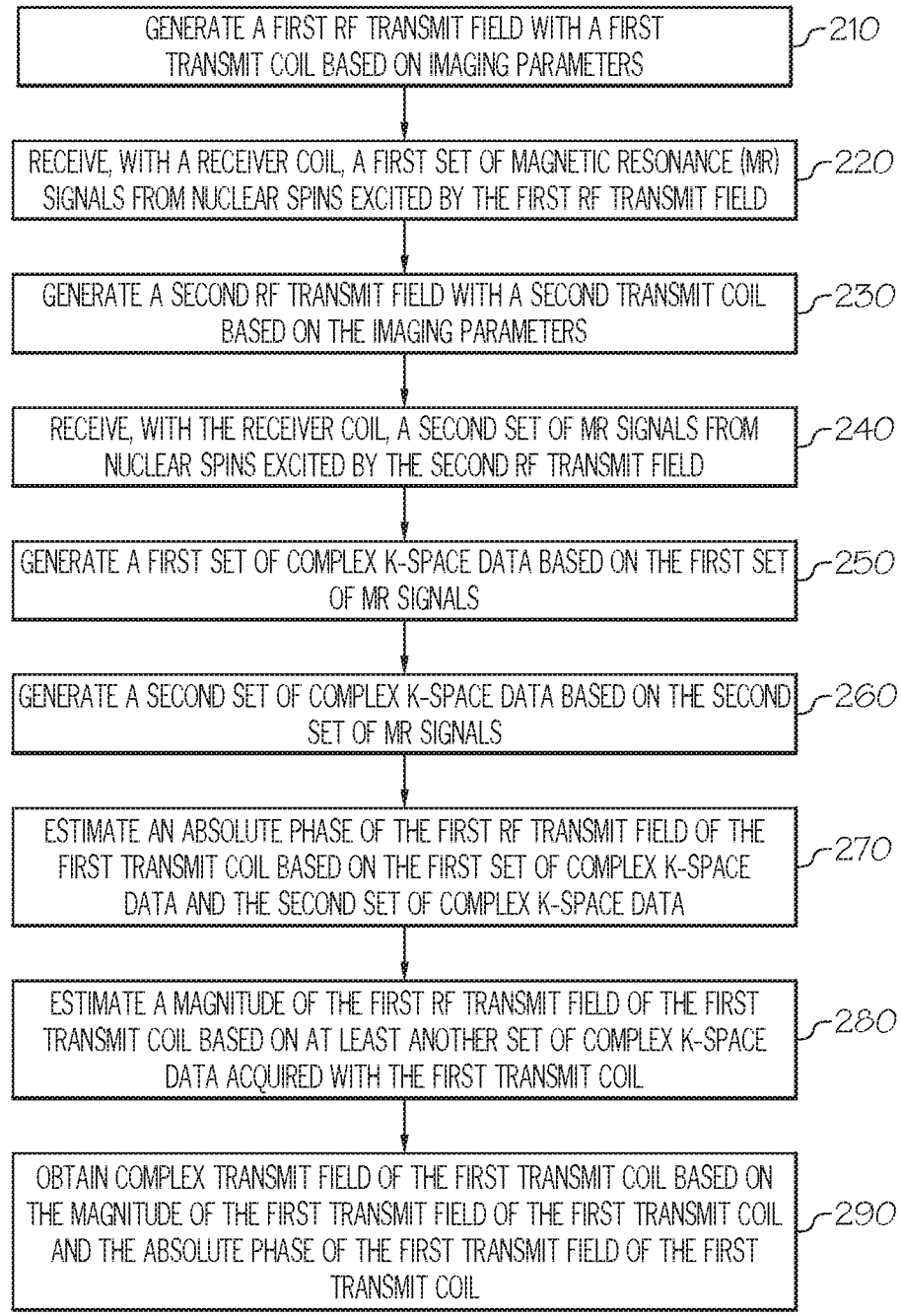
FIG. 2 is flowchart of estimating the absolute phase of transmit field $B_1^+$ of a transmit coil according to one or more embodiments described herein.

FIG. 2 is flowchart of estimating complex transmit field $B_1^+$ of a first transmit coil (i.e., a target transmit coil) with reference to a second transmit coil (i.e., a reference transmit coil) according to one or more embodiments shown and described herein.

In block 210, the MRI system 10 generate a first RF transmit field with a first transmit coil based on imaging parameters. In embodiments, the first transmit coil of the transmission and receiving unit 16 in FIG. 1 generates the first RF transmit field proximate to the target area 18 of the object 9 11. The first transmit coil may be, but not limited to one of surface coil, dual transmit coil, transceiver coil, transmit array coils, birdcage coil, single turn solenoid, saddle coil, and their variations.

In block 220, the MRI system 10 receives, with a receiver coil, a first set of magnetic resonance (MR) signals from nuclear spins excited by the first RF transmit field. In embodiments, the receiver coil of the transmission and receiving unit 16 receives the first set of MR signals from excited nuclear spins in the target area 18.

In block 230, the MRI system 10 generates a second RF transmit field with a second transmit coil based on the same imaging parameters as the ones used for the first transmit coil. In embodiments, the second transmit coil of the transmission and receiving unit 16 in FIG. 1 generates the second RF transmit field proximate to the target area 18 of the object 9. The first transmit coil may not be identical to the second transmit coil in structure and current distribution (e.g. current phase and amplitude). In some embodiments, the first transmit coil may have the same structure as the second transmit coil, but have different driven current phases. The second transmit coil may be, but not limited to one of surface coil, dual transmit coil, transceiver coil, transmit array coils, birdcage coil, single turn solenoid, saddle coil and their variations.

In embodiments, the second transmit coil may be shimmed or driven by adjusting a magnitude and/or a phase of current distribution in the second transmit coil such that the absolute phase of the second RF transmit field is significantly less than the absolute phase of the first RF transmit field. That is, the absolute phase of the second RF transmit field is ignorable, compared with the absolute phase of the first RF transmit field.

In block 240, the MRI system 10 receives, with the receiver coil, a second set of MR signals from nuclear spins excited by the second RF transmit field. In embodiments, the receiver coil of the transmission and receiving unit 16 receives the second set of MR signals from excited nuclear spins in the target area 18.

In block 250, the MRI system 10 generates a first set of complex k-space data based on the first set of MR signals. In embodiments, the MRI system 10 generates, in one k-space strategy, the first set of complex k-space data based on the first set of MR signals. The k-space strategy may be, but not limited to, a k-space sampling order, a k-space trajectory, a k-space under sampling, or a partial k-space acquisition. The k-space sampling order may be, but not limited to, at least one of a sequential sampling order, a centric sampling order, an interleave sampling order, a reverse sampling order, a random sampling order, or a hybrid sampling order.

In block 260, the MRI system 10 generates a second set of complex k-space data based on the second set of MR signals. In embodiments, the MRI system 10 generates, in one k-space strategy, the second set of complex k-space data based on the second set of MR signals. The MRI system 10 may use the same k-space strategy as the one used in block 250.

In block 270, the MRI system 10 estimates an absolute phase of the first RF transmit field of the first transmit coil based on the first set of complex k-space data and the second set of complex k-space data. In embodiments, the MRI system 10 transforms the first set of complex k-space data into a first complex image in an image domain, and transforms the second set of complex k-space data into a second complex image in an image domain. Then, the MRI system 10 estimates the absolute phase of the first RF transmit field of the first transmit coil based on the phase of the first complex image and the phase of the second complex image. Specifically, the MRI system 10 estimates the absolute phase of the first RF transmit field of the first transmit coil based on the following Equations (1)-(4).

A phase of a complex MR image is given:

$$\phi_{image} = \phi_T + \phi_{B0} + \phi_{Rec} + \phi_{syn} \qquad \text{Equation (1)}$$

Where $\phi_T$ is the absolute phase of the RF transmit field $B_1^+$ of a transmit coil. $\phi_{B0}$ is the phase accumulation of phases which result from at least one of $B_0$ inhomogeneity, flow, eddy current, and chemical shift. $\phi_{Rec}$ is a phase of a receiver coil which is a spatial function at the high field strength. $\phi_{syn}$ is a reference phase which is the sum of reference phases from transmitter radiofrequency synthesizer, receiver radiofrequency synthesizer, and digitizer. $\phi_{syn}$ is a constant, and thus, assumed to be zero.

For the first complex image acquired with the first transmit coil, the phase of the first complex image is given:

$$\phi_{image,1} = \Phi_1 + \phi_{B0} + \phi_{Rec} + \phi_{syn} \qquad \text{Equation (2)}$$

For the second image acquired with the second transmit coil, $$\phi_{image,2} = \Phi_2 + \phi_{B0} + \phi_{Rec} + \phi_{syn} \qquad \text{Equation (3)}$$

Since the second transmit coil is adjusted or configured to minimize its absolute phase as described above in block 230, the absolute phase $\Phi_2$ may be assumed to be ignorable. In this regard, the absolute phase $\Phi_1$ of the first transmit coil is given from Equations (2) and (3):

$$\Phi_1 = \phi_{image,2} - \phi_{image,1} \qquad \text{Equation (4)}$$

In block 280, the MRI system 10 estimates a magnitude of the first RF transmit field of the first transmit coil based on at least another set of complex k-space data acquired with the first transmit coil. In embodiments, the MRI system 10 acquires another set of complex k-space data based on the sets of MR signals which are excited by the first transmit coil based on different imaging parameters, and estimates a magnitude of the first RF transmit field of the first transmit coil based on the another set of complex k-space data.

In block 290, the MRI system 10 obtains complex transmit field of the first transmit coil based on the magnitude of the first transmit field of the first transmit coil and the absolute phase of the first transmit field and the first transmit coil.

Figure 3A:
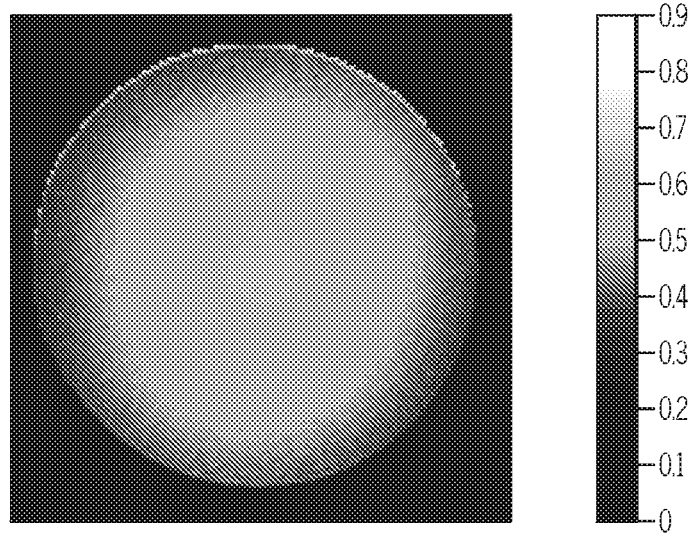
FIG. 3A illustrates an exemplary magnitude of $B_1^+$ of a birdcage coil with quadrature phase driven.
Figure 3B:
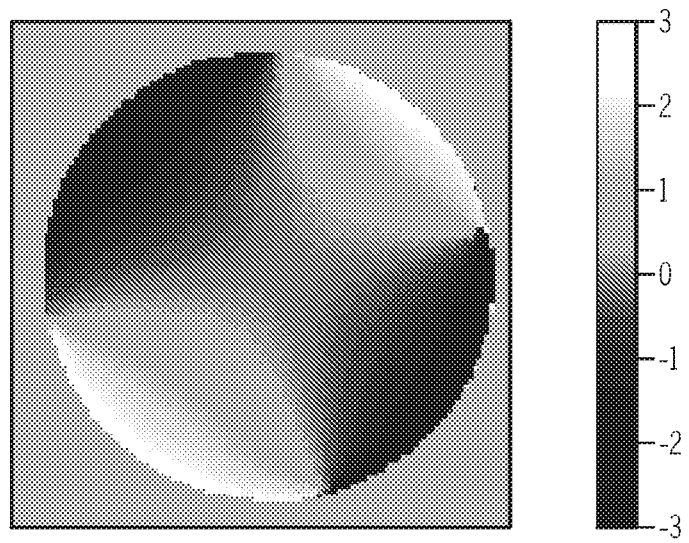
FIG. 3B illustrates an exemplary absolute phase of $B_1^+$ of a birdcage coil with quadrature phase driven.

FIGS. 3A and 3B illustrate an example for estimating complex RF transmit field $B_1^+$ of a birdcage coil with quadrature phase driven according to one or more embodiments shown and described herein. The transmit birdcage coil with the different phase combination may create three sub-coil configurations: (i) a linear mode in which channel 1 and channel 2 of birdcage coil have an identical phase; (ii) a quadrature mode in which the phase of channel 1 has a 90 degree phase shift from the phase of channel 2 to generate positive circularly polarized radiofrequency field; (iii) a reverse quadrature mode in which the phase of channel 1 has a 90 degree phase shift from the phase of channel 2 to generate negative circularly polarized radiofrequency field. Both the birdcage coil with quadrature phase driven and anti-quadrature phase driven are used to excite nuclear spins in magnetic resonance (MR) nuclei. The birdcage coil with anti-quadrature phase driven is used as a reference transmit coil. A receiver coil or array coils are used to detect MR signals arising from the birdcage coil with different current phase distribution, respectively. In embodiments, the receiver coil may be identical to one of the two transmit coils. In some embodiments, the receiver coil may not be identical to one of the two transmit coils.

The absolute phase of RF transmit field $B_1^+$ of the birdcage coil with quadrature phase driven (i.e., a target transmit coil) may be estimated directly or indirectly from the first set of complex k-space data and the second set of complex k-space data. For example, the two sets of complex k-space are transformed into two complex images in an image domain, and then the absolute phase of RF transmit field $B_1^+$ is estimated based on the two complex images, as described above with reference to Equation (4). The magnitude of $B_1^+$ of the birdcage coil with quadrature phase driven as shown in FIG. 3A is estimated by double flip angle method. In the double of flip angle method, two images are acquired gradient echo sequence with the birdcage coil with quadrature phase driven at the flip angles of 120 degrees and 60 degrees respectively. The signal intensity of these two images can be used to estimate the magnitude of $B_1^+$. The absolute phase of $B_1^+$ of the birdcage coil with quadrature phase driven as shown in FIG. 3B is estimated by the absolute phase of the birdcage coil as a reference. That is, two complex images are acquired by the birdcage coil with quadrature phase driven and anti-quadrature phase driven at the identical imaging parameters and receiver coil. The absolute phase of $B_1^+$ of the birdcage coil with quadrature phase driven is estimated by the difference of phase images of the two complex images.

In embodiments, a reference transmit coil with a minimal absolute phase of $B_1^+$ may be realized by a new coil configuration or by adjusting current distribution (e.g. magnitude or phase or both of current) of each element of the reference transmit coil to minimize absolute phase of $B_1^+$. For example, in order to estimate the absolute phase of a birdcage coil with quadrature driven mode (i.e., the first channel with phase of 0 degree and the second channel with phase of 90 degrees), a birdcage coil with anti-quadrature drive mode (i.e., the first channel with phase of 90 degrees and the second channel with phase of 0 degree) is introduced to as a reference transmit coil because the absolute phase of the birdcage transmit coil with anti-quadrature phase drive is assumed to be significantly less than that of the birdcage transmit coil with quadrature driven mode.

Estimating complex receiver sensitivity $B_1^-$ of a receiver coil

Figure 4:
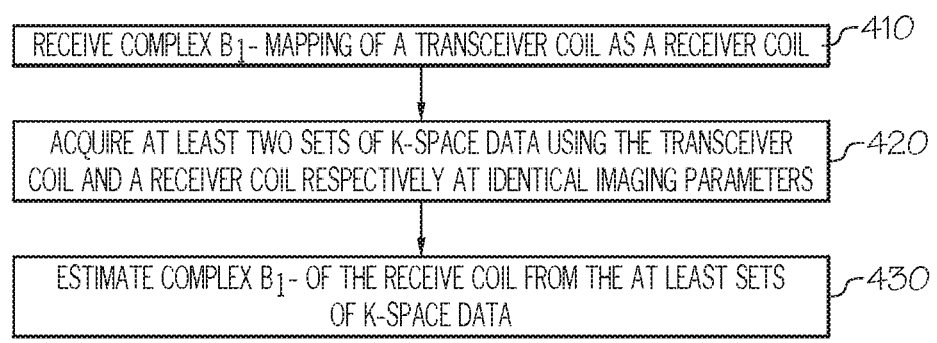
FIG. 4 is a schematic flowchart of estimating a spatial distribution of the complex receiver sensitivity $B_1^-$ of at least a portion of a receiver coil according to one or more embodiments shown and described herein.

FIG. 4 is a schematic flowchart of estimating a spatial distribution of the complex receiver sensitivity $B_1^-$ of at least a portion of a receiver coil according to one or more embodiments shown and described herein. In embodiments, the spatial distribution of the complex receiver sensitivity $B_1^-$ of at least a portion of a receiver coil is estimated based on the estimation of complex receiver sensitivity $B_1^-$ of a transceiver coil as a reference.

In block 410, the MRI system 10 receives complex receiver sensitivity $B_1^-$ mapping of a transceiver coil as a reference. The complex receiver sensitivity $B_1^-$ of the transceiver coil may be estimated using various methods, such as computer simulation and measurement from MRI images. One of the estimation methods is described below with reference to FIGS. 5 and 6.

In block 420, the MRI system 10 acquires at least two whole or part of k-space data within an imaged volume using both the transceiver coil as a receiver coil and the at least portion of the receiver coil. The at least two whole or part of k-space data are obtained based on the same transmit coil and imaging parameters. In order to reduce the scan time, various fast imaging techniques, such as parallel imaging acquisition, under-sampling acquisition, compensate sense, and simultaneous multiple-slice excitation, may be used to acquire the whole or part of k-space data.

In block 430, the MRI system 10 estimates complex receiver sensitivity $B_1^-$ of the at least portion of the receiver coil from the at least two sets of k-space data in either k-space domain or image domain. It is noted that at least one image k-space data with the receiver coil is obtained under the same imaging parameters as the ones used for obtaining at least one image acquired with the transceiver coil. The magnitude and phase of $B_1^-$ mapping of the receiver coil may be estimated from the at least two k-space data sets. For example, the at least two k-space data sets may be used to reconstruct at least two images respectively. And then, the magnitude and phase of $B_1^-$ mapping of the receiver coil is calculated by complex receiver sensitivity $B_1^-$ of the transceiver coil and a ratio of the two images which are respectively acquired with the transceiver coil and the receiver coil under the same imaging parameter and sequence. The complex receiver sensitivity $B_1^-$ image may be stored in a memory.

Figure 5:
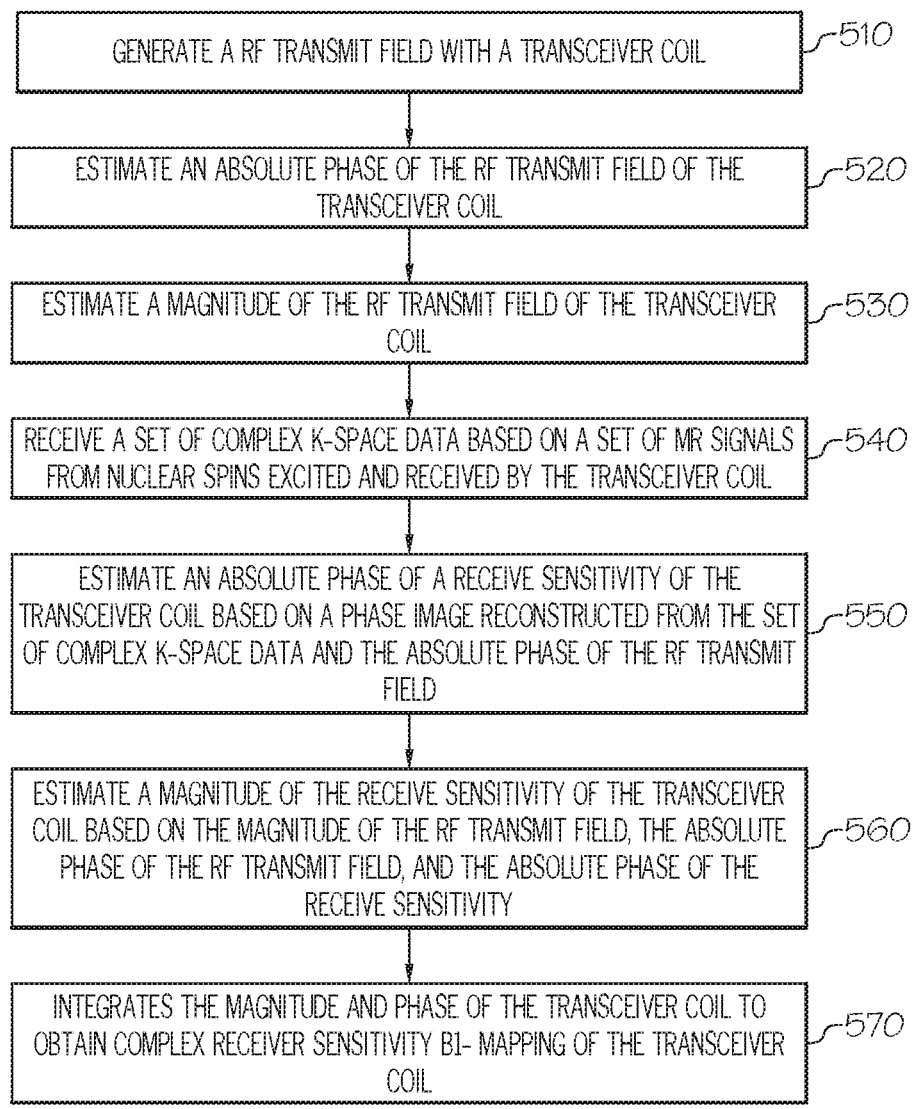
FIG. 5 is a schematic flowchart of estimating a spatial distribution of the complex receiver sensitivity $B_1^-$ of a transceiver coil from the complex transmit field $B_1^+$ of the transceiver coil according to one or more embodiments shown and described herein.

FIG. 5 is a schematic flowchart of estimating complex receiver sensitivity $B_1^-$ mapping of a transceiver coil from the complex transmit field $B_1^+$ of the transceiver coil, according to one or more embodiments shown and described herein.

In block 510, the MRI system 10 generates a RF transmit field with a transceiver coil. In embodiments, the transceiver coil of the transmission and receiving unit 16 in FIG. 1 generates the RF transmit field proximate to the target area 18 of the object 9. The transceiver coil may be, but not limited to one of surface coil, dual transmit coil, transceiver coil, transmit array coils, birdcage coil, single turn solenoid, saddle coil and their variations.

In block 520, the MRI system 10 estimates an absolute phase of the RF transmit field of the transceiver coil. Many methods, including the method described above with reference to block 270 in FIG. 2 may be used to estimate the absolute phase of the RF transmit field of the transceiver coil.

In block 530, the MRI system 10 estimates a magnitude of the RF transmit field of the transceiver coil. Many methods, including the method described above with reference to block 280 in FIG. 2 may be used to estimate the magnitude of the RF transmit field of the transceiver coil.

In block 540, the MRI system 10 receives a set of complex k-space data based on a set of MR signals from nuclear spins excited and received by the transceiver coil. In embodiments, the transceiver coil receives MR signals from the excited nuclear spins and the MRI system 10 transforms the MR signals to the set of complex k-space data.

In block 550, the MRI system estimates an absolute phase of a receiver sensitivity of the transceiver coil based on a phase image reconstructed from the set of complex k-space data and the absolute phase of the RF transmit field of the transceiver coil.

In embodiments, in order to minimize the effect of $B_0$ inhomogeneity, some sequences, such as spin echo, steady state free precession, ultra-short echo time, and zero echo time sequences, are used to simplify Equation (1) as:

$$\phi_{image} = \phi_T + \phi_{Rec} + \phi_{syn} \quad \text{Equation (5)}$$

where $\phi_{image}$ is an absolute phase of the complex MR image acquired with at least one of spin echo, steady state free precession, ultra-short echo time, and zero echo time sequences. The complex MR image is reconstructed from the set of complex k-space data obtained in block 540. $\phi_T$ is the absolute phase of the transceiver coil. Reference phase $\phi_{syn}$ is set to zero. Thus, the absolute phase of the receiver sensitivity $B_1^-$ of the transceiver coil is given from (5):

$$\phi_{Rec} = \phi_{image} - \phi_T \quad \text{Equation (6)}$$

In block 560, the MRI system 10 estimates a magnitude of the receiver sensitivity of the transceiver coil based on the magnitude of the RF transmit field, the absolute phase of the RF transmit field, and the absolute phase of the receiver sensitivity.

When the transceiver coil is used as a transmit coil or a transmit antennas, the transmit electromagnetic field and their components will be complex variables which may be assumed as:

$$B_{xt} = a + ib \quad \text{Equation (7a)}$$

$$B_{yt} = c + id \quad \text{Equation (7b)}$$

Where a, b, c, and d are real variables. And i is the imaginary unit or unit imaginary number.

When the transceiver coil is used as a receiver coil or a receiver antennas, the receive magnetic flux density $\vec{B}_r = \vec{B}_t$ according to the reciprocity principle of electromagnetic field. That is, $$B_{xr} = a + ib \quad \text{Equation (8a)}$$

$$B_{yr} = c + id \quad \text{Equation (8b)}$$

Where $B_{xr}$ and $B_{yr}$ are complex components of $\vec{B}_r$ at the directions of x and y, respectively.

Transmit field of the transceiver source as a transmitter for MRI is given by $$B_1^+ = \frac{B_{xt} - iB_{yt}}{\sqrt{2}} = \frac{(a+d) + i(b-c)}{\sqrt{2}} = |B_1^+|e^{i\varphi_t} \quad \text{Equation (9a)}$$

Receiver sensitivity of the transceiver source as a receiver for MRI is given by $$B_1^- = \frac{B_{xt} + iB_{yt}}{\sqrt{2}} = \frac{(a-d) + i(b+c)}{\sqrt{2}} = |B_1^+|e^{i\varphi_t} \quad \text{Equation (9b)}$$

According to the Equations (9a) and (9b), the real part of transmit field and receiver sensitivity are identical, which is reduced to:

$$|B_1^+|\cos\varphi_t = |B_1^-|\cos\varphi_r \quad \text{Equation (10)}$$

From Equation (10), the receiver sensitivity is obtained by $$|B_1^-| = \frac{|B_1^+|\cos\varphi_t}{\cos\varphi_r} \quad \text{Equation (11)}$$

The computer simulation of MR image and MRI experiments confirmed that the magnitude of receiver sensitivity $B_1^-$ is proportional to the magnitude of the circularly polarized component of the $B_1$ field that rotates in the direction opposite to that of nuclear precession.

It is noted that the absolute phase should be zero at low radiofrequency field because the wave effect may be ignorable. In that case, transmit field and receiver sensitivity may be described by real variables or numbers. Thus, Equation (11) is reduced to $|B_1^+| = |B_1^-|$.

In block 570, the MRI system 10 integrates the magnitude and phase of the receiver sensitivity of the transceiver coil to obtain complex receiver sensitivity $B_1^-$ mapping of the transceiver coil.

Figure 6:
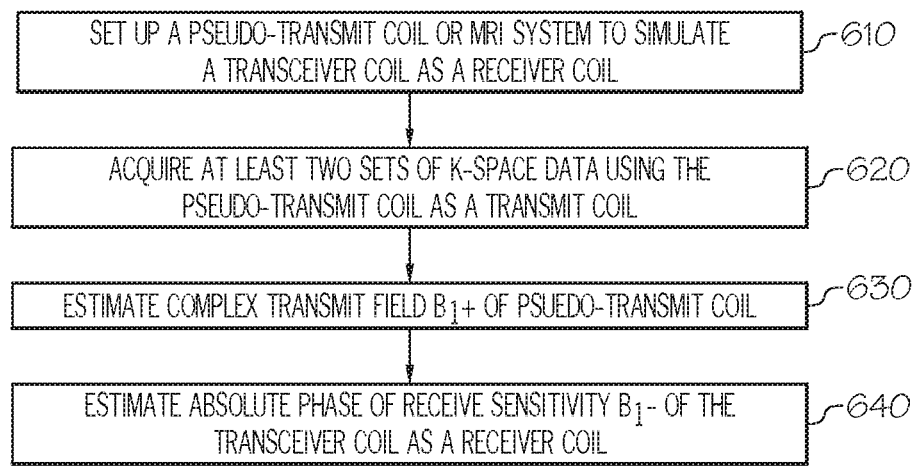
FIG. 6 is a schematic flowchart of estimating complex $B_1^-$ mapping of a transceiver coil from a pseudo-transition coil in an MRI system, according to one or more embodiments shown and described herein.

FIG. 6 is a schematic flowchart of estimating a spatial distribution of the complex receiver sensitivity $B_1^-$ of a transceiver coil from a pseudo-transition coil in a MRI system, according to one or more embodiments shown and described herein.

In block 610, a pseudo-transition is set up to simulate the transceiver coil as a receiver coil. The pseudo-transition includes a pseudo-transition coil and the same subject being imaged with the transceiver coil.

In block 620, at least two whole or part of k-space data are acquired with the pseudo-transition coil as a transmit coil. In order to reduce the scan time, various fast imaging techniques, such as parallel imaging acquisition, under-sampling acquisition, compensate sense, and simultaneous multiple-slice excitation, may be used to acquire the whole or part of k-space data.

In block 630, the MRI system estimates the complex RF transmit field $B_1^+$ of the pseudo-transition coil from the k-space data. The method of estimating the complex RF transmit field $B_1^+$ of the pseudo-transition coil is described above with reference to FIG. 2.

In block 640, complex radio frequency (RF) receiver sensitivity $B_1^-$ of the transceiver coil as a receiver coil equals to the complex transmit field $B_1^+$ of the pseudo-transition coil. Thus, complex radio frequency (RF) receiver sensitivity $B_1^-$ of the transceiver coil may be estimated from the complex transmit field $B_1^+$ of the pseudo-transition coil estimated in block 630. Finally, the complex receiver sensitivity $B_1^-$ of the transceiver coil is stored in a memory.

The computer simulation of MR image and MRI experiments confirmed that the magnitude of receiver sensitivity $B_1^-$ is proportional to the magnitude of the circularly polarized component of the $B_1$ field that rotates in the direction opposite to that of nuclear precession. The features of a transceiver coil as a receiver coil may be simulated by a pseudo-transmit coil. In embodiments, the coil configuration of the pseudo-transmit coil may be identical to the transceiver coil, but the pseudo-transmit coil may be driven by the current which is opposite to that of the transceiver coil as a transmit coil. The absolute phase of the pseudo-transmit coil may be estimated according to the method described above with reference to FIG. 2. The magnitude of pseudo-transmit coil may be estimated by various methods, such as dual angle method, actual flip angle imaging method, dual refocusing echo acquisition mode (DREAM), phase Sensitive method, Bloch-Siegert method, but not limited to, adiabatic Bloch-Siegert method. The magnitude and the phase of the transceiver coil equal to those of pseudo-transmit coil respectively.

Figure 7:
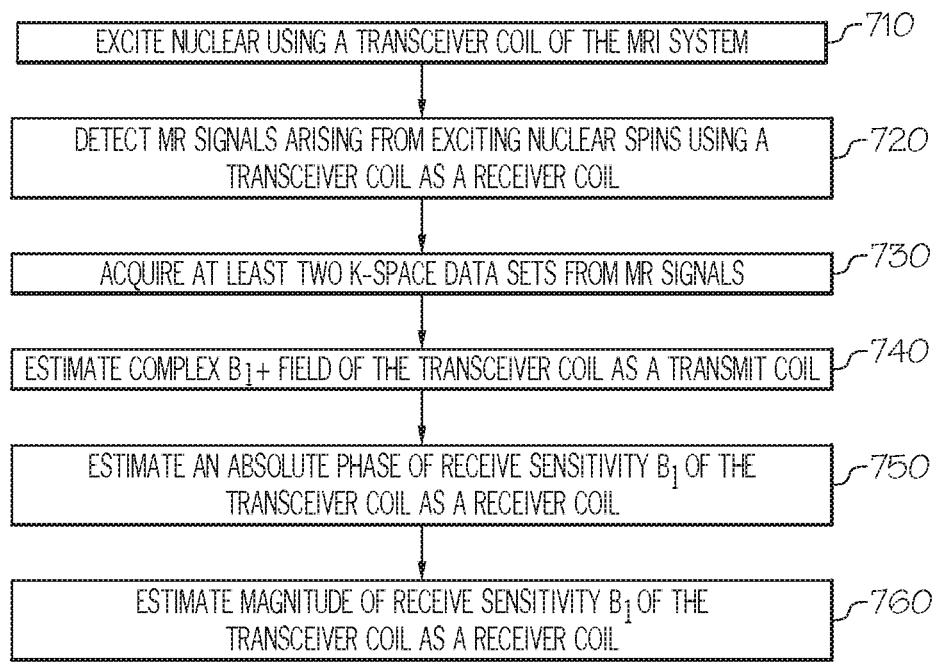
FIG. 7 is a schematic flowchart of illustrating example operations for determining spatial distribution of complex receiver sensitivity $B_1^-$ of a transceiver coil in an MRI system from complex transmit field $B_1^+$ mapping of the transceiver coil.

Referring now to FIG. 7, a flowchart illustrating example operations for estimating complex $B_1^-$ mapping of a transceiver coil from the complex $B_1^+$ mapping of the transceiver coil is shown.

In block 710, nuclear spins in magnetic resonance (MR) are excited using a transceiver coil of the MRI system. In embodiments, the transceiver coil of the transmission and receiving unit 16 in FIG. 1 generates a RF transmit field which excites nuclear spins in the target area 18 of the object 9.

In block 720, MR signals arising from excited nuclear spins in MR nuclei is detected using the transceiver coil of the MRI system as a receiver coil. In embodiments, the transceiver coil of the transmission and receiving unit 16 detects MR signals arising from the excited nuclear spins.

In block 730, the MRI system 10 acquires at least two sets of complex k-space data from the MR signals. In embodiments, the MRI system 10 acquires a first set of complex k-space data from MR signals from nuclear spins excited by the transceiver coil, and acquires a second set of complex k-space data from MR signals from nuclear spins excited by a reference transmit coil.

In block 740, the complex transmit filed $B_1^+$ of the transceiver coil as a transmit coil of the MRI system is estimated. As discussed herein, this information may be obtained, for example, using the techniques described above with reference to FIG. 2 or alternatively using any other known technique.

In block 750, the absolute phase of receiver sensitivity $B_1^-$ of the transceiver coil as a receiver coil is estimated using the absolute phase of the transmit field $B_1^+$ of the transmit coil of the MRI system and at least one of the complex image obtained using the transceiver coil or the phase of the complex image. For example, as described above, the absolute phase of receiver sensitivity $B_1^-$ of the receiver coil may be estimated using Equation (6) described above.

In block 760, the magnitude of the receiver sensitivity $B_1^-$ of the transceiver coil as a receiver coil is estimated from the complex transmit field $B_1^+$ of the transceiver coil and the absolute phase of the receiver sensitivity $B_1^-$ of the receiver coil. For example, as described above with reference to FIG. 5, the magnitude of the receiver sensitivity $B_1^-$ of the transceiver coil may be estimated using Equation (11) described above.

Figure 8:
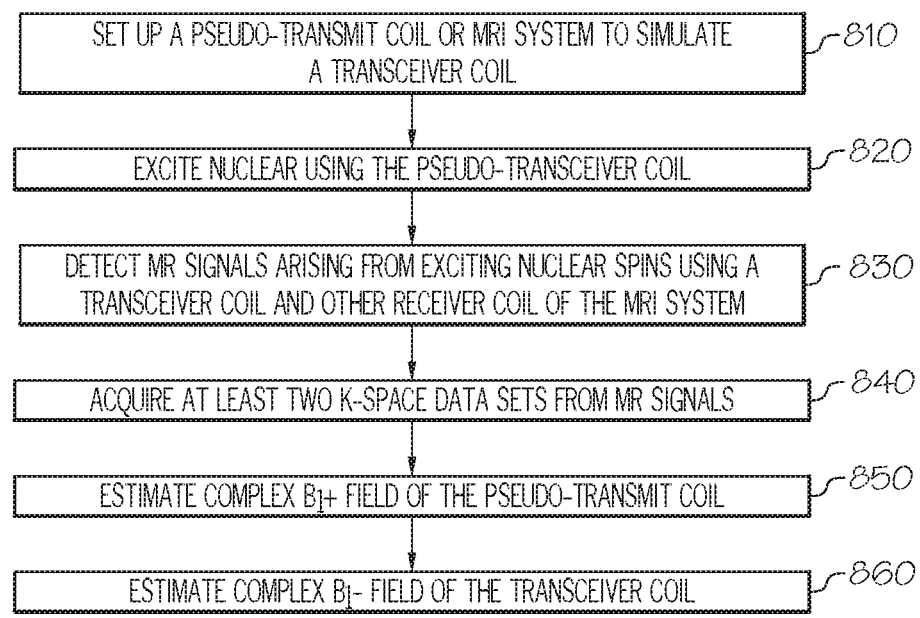
FIG. 8 is a schematic flowchart of illustrating example operations for determining spatial distribution of complex RF receiver sensitivity $B_1^-$ of a transceiver coil in an MRI system from complex transmit field $B_1^+$ mapping of a pseudo-transition coil.

FIG. 8 depicts a flowchart illustrating example operations for estimating complex $B_1^-$ mapping of a transceiver coil from a pseudo-transmit coil, according to one or more embodiments shown and described herein.

In block 810, the MRI system sets up a pseudo-transit coil to simulate a transceiver coil.

In block 820, nuclear spins in magnetic resonance (MR) nuclei may be excited using a pseudo transition coil of the MRI system. The pseudo-transition includes a pseudo-transition coil and the same object is imaged with the transceiver coil as a receiver coil.

In block 830, the MR system detects MR signals arising from nuclear spins in MR nuclei excited by a transceiver coil of the MRI system, and detects MR signals arising from nuclear spins in MR nuclei excited by another transmit coil of the MRI system.

In block 840, the MR system acquires at least two sets of complex k-space data from the MR signals. In embodiments, the MR system acquires a first set of complex k-space data arising from the MR signals arising from nuclear spins excited by the transceiver coil, and a second set of complex k-space data arising from the MR signals arising from nuclear spins excited by the transmit coil.

In block 850, complex transmit field $B_1^+$ (e.g. magnitude and absolute phase) of the pseudo-transmit coil of the MRI system is estimated. As discussed herein, this information may be obtained, for example, using the techniques described above with reference to FIG. 2 or alternatively using any other known technique.

In block 860, complex receiver sensitivity $B_1^-$ mapping of a transceiver coil is estimated from the complex $B_1^+$ mapping of the pseudo-transmit coil. For example, complex receiver sensitivity $B_1^-$ field of the transceiver coil may be equal to the complex transmit field $B_1^+$ of the pseudo-transmit coil according to the definition of $B_1^+$ and $B_1^-$ of the transceiver coil. That is, $B_1^+$ is the positive circularly polarized component of a transversal transmit field of a RF pulse which is generated by the transceiver coil, and $B_1^-$ is the negative circularly polarized component of a transversal receiver field of the transceiver coil. For example, if the main magnetic field is inversed, the complex transmit field $B_1^+$ before the main magnetic field is inversed would be equal to receiver sensitivity $B_1^-$ after the main magnetic field is inversed. Therefore, complex receiver sensitivity $B_1^-$ mapping of the transceiver coil may be estimated from the transmit field of the pseudo-transmit coil.

Figure 9A:
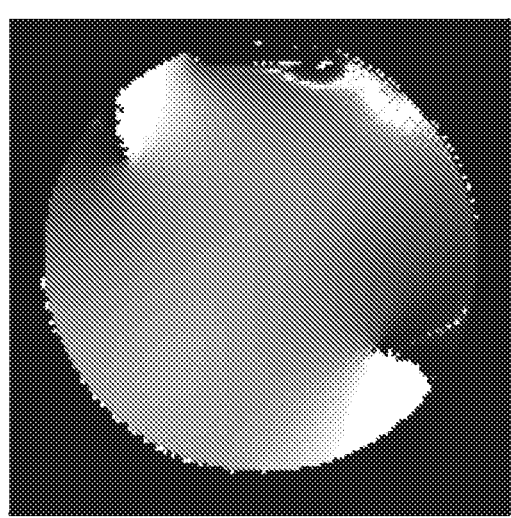
FIG. 9A illustrates an exemplary magnitude of $B_1^-$ of a body coil in a dual transmit coil system.
Figure 9B:
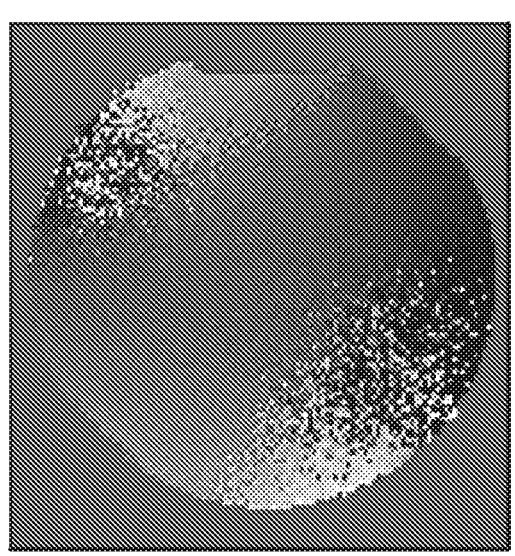
FIG. 9B illustrates an exemplary absolute phase of $B_1^-$ of a body coil in a dual transmit coil system.

FIGS. 9A and 9B illustrate an example for estimating complex RF receive sensitivity $B_1^-$ of a transceiver coil according to one or more embodiments shown and described herein. The images are acquired with a transceiver coil as a transmitter and a receiver. The absolute phase image of $B_1^+$ of the transmit coil is estimated using method described in one or more embodiments shown and described herein. The absolute phase image of receiver sensitivity $B_1^-$ of the receiver coil as shown in FIG. 9B is estimated by Equation (6) using the phase image acquired with spin echo sequence and the absolute phase image of $B_1^+$ of the transmit coil. The magnitude of receive sensitivity $B_1^-$ as shown in FIG. 9A may be estimated by Equation (11) using complex transmit field $B_1^+$ and the absolute phase image of receiver sensitivity $B_1^-$. That is, the complex RF receive sensitivity $B_1^-$ of the transceiver coil as a receiver coil is estimated from the complex $B_1^+$ of the transceiver coil as the receiver coil.

In another embodiment, the estimated complex $B_1^-$ map in the k-space domain of at least a portion of a receiver coil of the MRI system may be obtained by whole or part of k-space data. For example, complex receiver sensitivity $B_1^-$ map may be optionally estimated using the center of k-space data since $B_1^-$ map changes smoothly and slowly in MRI system.

The estimated complex receiver sensitivity $B_1^-$ may be used for various applications. In embodiments, the estimated complex receiver sensitivity $B_1^-$ may be used for combining a plurality of signals acquired with each of a plurality of coil elements in a coil array of the MRI or MRS system. In some embodiments, the estimated complex receiver sensitivity $B_1^-$ may be used for performing at least one of an MRI image reconstruction algorithm or reducing artifacts in parallel image acquisition. For example, the parallel image acquisition can be performed using at least one of SENSE, PARS, SMASH, or GRAPPA methods. Optionally, parallel image acquisition signals are acquired using a Cartesian or non-Cartesian k-space trajectory. In some embodiments, the estimated complex receiver sensitivity $B_1^-$ may be used for quantifying various parameters. For example, the estimated complex receiver sensitivity $B_1^-$ may be used to reduce MR signal inhomogeneity caused by the at least the portion of the receiver coil of the MRI system. The estimated complex receiver sensitivity $B_1^-$ may be used to quantify various tissue electrical properties, such as a conductivity of a sample, a permeability of the sample, or an electromagnetic field distribution inside the sample. For example, determining at least one of the conductivity or the permeability of the sample provides a biomarker for functional MRI, a diagnosis of disease, electromagnetic therapy, or human safety in electromagnetic environment. Additionally, the estimated complex receiver sensitivity $B_1^-$ may be used to perform quantitative MRI or quantitative magnetic resonance spectroscopy (MRS) with an external or internal reference. Additionally, parallel transmit techniques may optionally be derived from an amplitude and a phase of the $B_1^-$ map of the MRI system.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A method for determining spatial distribution of a complex radio frequency (RF) transmit field in a magnetic resonance imaging (MRI) system, comprising:
generating a first RF transmit field with a first transmit coil based on imaging parameters;
receiving, with a receiver coil, a first set of magnetic resonance (MR) signals from nuclear spins excited by the first RF transmit field;
generating a second RF transmit field with a second transmit coil based on the imaging parameters;
receiving, with the receiver coil, a second set of MR signals from nuclear spins excited by the second RF transmit field;
generating a first set of complex k-space data based on the first set of MR signals;
generating a second set of complex k-space data based on the second set of MR signals; and
estimating an absolute phase of the first RF transmit field of the first transmit coil based on the first set of complex k-space data and the second set of complex k-space data;
estimating a magnitude of the first RF transmit field of the first transmit coil based on at least another set of complex k-space data acquired with the first transmit coil;
displaying an MRI image on an output device based on MR signals,
wherein an absolute phase of the second RF transmit field is significantly less than an absolute phase of the first RF transmit field, and
wherein the second transmit coil is shimmed or driven by adjusting a magnitude and/or a phase of current distribution in the second transmit coil such that an absolute phase of the second RF transmit field is ignorable compared to an absolute phase of the first RF transmit field.

2. A method for determining a spatial distribution of complex receiver sensitivity of a transceiver coil in a magnetic resonance imaging (MRI) system, comprising:
generating a RF transmit field with a transceiver coil;
estimating an absolute phase of the RF transmit field of the transceiver coil;
estimating a magnitude of the RF transmit field of the transceiver coil;
receiving a set of complex k-space data based on a set of MR signals from nuclear spins excited and received by the transceiver coil;
estimating an absolute phase of a receiver sensitivity of the transceiver coil based on a phase image reconstructed from the set of complex k-space data and the absolute phase of the RF transmit field;
estimating a magnitude of the receiver sensitivity of the transceiver coil based on the magnitude of the RF transmit field, the absolute phase of the RF transmit field, and the absolute phase of the receiver sensitivity; and
displaying an MRI image on an output device based on MR signals.

3. A magnetic resonance imaging (MRI) system for determining spatial distribution of the complex receiver sensitivity of a transceiver coil in a magnetic resonance imaging (MRI) system, the MRI system comprising:
a transceiver coil;
a processing unit;
a system memory; and
machine readable instructions stored in the system memory that, when executed by the processing unit, cause the MRI system to:
generate a RF transmit field with the transceiver coil;
estimate an absolute phase of the RF transmit field of the transceiver coil;
estimate a magnitude of the RF transmit field of the transceiver coil;
generate a set of complex k-space data based on a set of MR signals from nuclear spins excited by the RF transmit field;
estimate an absolute phase of a receiver sensitivity of the transceiver coil based on a phase image reconstructed from the set of complex k-space data and the absolute phase of the RF transmit field; and
estimate a magnitude of the receiver sensitivity of the transceiver coil based on the magnitude of the RF transmit field, the absolute phase of the RF transmit field, and the absolute phase of the receiver sensitivity.

4. The method of claim 1, wherein the absolute phase of the second RF transmit field is ignorable compared to the absolute phase of the first RF transmit field.

5. The method of claim 1, wherein the second transmit coil is any transmit configuration with optimal current distribution such that an absolute phase of the second RF transmit field is ignorable compared to an absolute phase of the first RF transmit field.

6. The method of claim 1, further comprising:
transforming the first set of complex k-space data into a first complex image in an image domain;
transforming the second set of complex k-space data into a second complex image in an image domain,
transforming at least another set of complex k-space data acquired with the first transmit coil into a third complex image in an image domain,
wherein the absolute phase of the first RF transmit field and the magnitude of the first RF transmit field are estimated based on the first complex image, the second complex image and the third complex image.

7. The method of claim 1, wherein the first transmit coil comprises at least one of surface coil, dual transmit coil, transceiver coil, transmit array coils, birdcage coil, single turn solenoid, or, or saddle coil.

8. The method of claim 1, where the magnitude of the first RF transmit field of the first transmit coil is estimated by at least one of a double flip angle, but not limited to, or an actual flip angle, or phase sensitive method, or dual refocusing echo acquisition mode (DREAM), or Bloch-Siegert method, or adiabatic Bloch-Siegert method.

9. The method of claim 2, further comprising
simulating the transceiver coil as a receiver coil with a pseudo-transition coil;
acquiring at least two whole or part of k-space data using the pseudo-transition coil within an imaged volume;
estimating a complex RF transmit field of the pseudo-transition coil based on the at least two whole or part of k-space data; and
obtaining a magnitude and/or phase of the receiver sensitivity of the transceiver coil based on the complex RF transmit field of the pseudo-transition coil.

10. The method of claim 2, further comprising:
acquiring at least two whole or part of k-space data using both the transceiver coil as a receiver coil and at least portion of a receiver coil; and
estimating complex receiver sensitivity of the at least portion of the receiver coil based on the at least two whole or part of k-space data.

11. The method of claim 10, wherein the complex receiver sensitivity of the receiver coil is calculated based on the complex receiver sensitivity of the transceiver coil and a ratio of two images that are acquired with the transceiver coil and the receiver under the same imaging parameters and sequence.

12. The method of claim 2, further comprising:
applying the complex RF receiver sensitivity of the transceiver coil to perform MRI image reconstruction in parallel image acquisition.

13. The method of claim 12, wherein the parallel image acquisition is performed using at least one of SENSitivity Encoding (SENSE), Parallel magnetic resonance imaging with Adaptive Radius in k-Space (PARS), SiMultaneous Acquisition of Spatial Harmonics (SMASH), but not limited to, or GeneRalized Autocalibrating Partial Parallel Acquisition (GRAPPA).

14. The method of claim 2, further comprising:
applying complex receiver sensitivity to estimate changes of electromagnetic field caused by an electromagnetic property of an object being imaged; and
applying complex receiver sensitivity to combine a plurality of images acquired with each of a plurality of coil elements in a coil array of the MRI system.

15. The method of claim 2, wherein the complex receiver sensitivity includes information about associating an estimated electrical property with a pathological state of tissues in an object being imaged.

16. The method of claim 2, further comprising:
determining specific energy absorption rate (SAR) based on the magnitude and the absolute phase of the receiver sensitivity.

17. The method of claim 2, further comprising:
correcting MR signal inhomogeneity caused by receiver coils of the MRI system based on the magnitude and the absolute phase of the receiver sensitivity.

18. The method of claim 1, wherein imaging sequences for both estimating complex transmit field and receiver sensitivity comprises including at least one of gradient echo-based sequences, spin-echo-based sequences, echo planar imaging (EPI) based sequences, or ultra-short echo time sequences; and
wherein fast imaging techniques including at least one of parallel imaging acquisition, under-sampling acquisition, compensate sense, or simultaneous multiple-slice excitation are employed.

19. The MRI system of claim 3, further comprising:
a pseudo-transition coil configured to simulate the transceiver coil as a receiver coil,
wherein the machine readable instructions stored in the system memory, when executed by the processing unit, cause the MRI system to:
acquire at least two whole or part of k-space data using the pseudo-transition coil within an imaged volume;
estimate a complex RF transmit field of the pseudo-transition coil based on the at least two whole or part of k-space data; and
obtain a magnitude and/or phase of the receiver sensitivity of the transceiver coil based on the complex RF transmit field of the pseudo-transition coil.

* * * * *

UNITED STATES PATENT AND TRADEMARK OFFICE
CERTIFICATE OF CORRECTION

PATENT NO. : 11,579,219 B2
APPLICATION NO. : 16/753990
DATED : February 14, 2023
INVENTOR(S) : Jinghua Wang Page 1 of 1

It is certified that error appears in the above-identified patent and that said Letters Patent is hereby corrected as shown below:

On the Title Page

In page 2, Column 2, Item (56) cite no. 1, delete "Dsing" and insert --Using--, therefor.

In page 2, Column 2, Item (56) cite no. 7, delete "Phse" and insert --Phase--, therefor.

In page 2, Column 2, Item (56) cite no. 7, delete "Tramit" and insert --Transmit--, therefor.

In the Specification

In Column 14, Line(s) 64, after "can equal to", delete "BC" and insert --$\mathbf{B_1}^-$--, therefor.

Signed and Sealed this
Twenty-fifth Day of July, 2023

Katherine Kelly Vidal
*Director of the United States Patent and Trademark Office*